(12) United States Patent
Schmidt et al.

(10) Patent No.: US 9,597,429 B2
(45) Date of Patent: *Mar. 21, 2017

(54) CELL-FREE TISSUE REPLACEMENT FOR TISSUE ENGINEERING

(71) Applicant: Board of Regents, The University of Texas System, Austin, TX (US)

(72) Inventors: Christine E. Schmidt, Austin, TX (US); Terry Hudson, Foster City, CA (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/274,156

(22) Filed: May 9, 2014

(65) Prior Publication Data

US 2014/0248325 A1    Sep. 4, 2014

Related U.S. Application Data

(63) Continuation of application No. 12/135,772, filed on Jun. 9, 2008, now Pat. No. 8,758,794, which is a continuation of application No. 10/672,689, filed on Sep. 26, 2003, now Pat. No. 7,402,319.

(60) Provisional application No. 60/414,278, filed on Sep. 27, 2002.

(51) Int. Cl.
*A61L 27/36* (2006.01)
*A61L 27/38* (2006.01)

(52) U.S. Cl.
CPC ....... *A61L 27/3633* (2013.01); *A61L 27/3604* (2013.01); *A61L 27/3675* (2013.01); *A61L 27/3687* (2013.01); *A61L 27/383* (2013.01); *A61L 27/3878* (2013.01); *A61L 2430/40* (2013.01)

(58) Field of Classification Search
None
See application file for complete search history.

(56) References Cited

U.S. PATENT DOCUMENTS

| | | |
|---|---|---|
| 4,372,888 A | 2/1983 | Hjelmeland |
| 4,505,266 A | 3/1985 | Yannas et al. |
| 4,776,853 A | 10/1988 | Klement et al. |
| 5,336,616 A | 8/1994 | Livesey et al. |
| 5,543,498 A | 8/1996 | Fishman et al. |
| 5,613,982 A | 3/1997 | Goldstein |
| 5,716,411 A | 2/1998 | Orgill et al. |
| 5,843,892 A | 12/1998 | Patterson et al. |
| 5,898,000 A | 4/1999 | Matsuda et al. |
| 5,919,196 A | 7/1999 | Bobic et al. |
| 5,962,434 A | 10/1999 | Schnaar et al. |
| 5,968,905 A | 10/1999 | Patterson |
| 6,004,771 A | 12/1999 | Thornton |
| 6,080,753 A | 6/2000 | Lyons et al. |
| 6,207,451 B1 | 3/2001 | Dennis et al. |
| 6,290,718 B1 | 9/2001 | Grooms et al. |
| 6,352,557 B1 | 3/2002 | Ferree |
| 6,371,992 B1 | 4/2002 | Tanagho et al. |
| 6,376,244 B1 | 4/2002 | Atala |
| 6,376,742 B1 | 4/2002 | Zdrahala et al. |
| 6,398,819 B1 | 6/2002 | Bell |
| 6,448,076 B2 | 9/2002 | Dennis et al. |
| 6,613,278 B1 | 9/2003 | Mills et al. |
| 6,734,018 B2 | 5/2004 | Wolfinbarger, Jr. et al. |
| 6,783,776 B2 * | 8/2004 | Spievack ............ 424/558 |
| 7,122,205 B2 * | 10/2006 | Peterson et al. ........ 424/486 |
| 7,402,319 B2 | 7/2008 | Schmidt et al. |
| 7,541,187 B2 * | 6/2009 | Myles et al. ............ 435/395 |
| 8,758,794 B2 * | 6/2014 | Schmidt et al. .......... 424/423 |
| 2001/0000804 A1 | 5/2001 | Goldstein et al. |

OTHER PUBLICATIONS

Bruck, W. "The Role of Macrophages in Wallerian Degeneration" (1997) Brain Pathol 7. 741-752.
Chamberlain, et al., "Collagen-GAG Substrate Enhances the Quality of Nerve Regeneration through Collagen Tubes up to Level of Autograph." Exp Neurol (1993), 154:315-329.
Chamberlain, et al , "Near-Terminus Axonal Structure and Function Following Rat Sciatic Nerve Regeneration Through a Collagen-GAG Matrix in a Ten-Millimeter Gap." J. Neurosci Res (2000), 60:666-677.
Danielsen, et al. "Predegeneration enhances regeneration into acellular nerve grafts" (1995) Brain Res 681, 105-108.
Dow Chemical Company. "TRITON™ X-200K Surfactant. Chemical Description", Form No. 119-01882-1207.
Dumont, et al., "Enhancement of Axon Growth by Detergent-Extracted Nerve Grafts," Transplantation (May 15, 1997), 63:1210-1215.
Evans, et al., "Ther Peripheral Ferve Allograft: a Comprehensive Review of Regeneration and Neruoimmunology." Prog Neurobiol (1994), 43:187-233.
Fawcett, et al. "Peripheral Nerve Regeneration" (1990) Annu Rev Neurosci 13, 43-60.
Frostick, et al, "Schwann Cells, Neurotrophic Factors, and Peripheral Nerve Regeneration" (1998) Microsurgery 18, 397-405.

(Continued)

*Primary Examiner* — Janice Li
(74) *Attorney, Agent, or Firm* — Edwin S. Flores; Daniel J. Chalker; Chalker Flores, LLP

(57) ABSTRACT

The present invention is a natural, cell-free tissue replacement that does not require difficult or extensive preparation made by washing tissue replacement in a solution including one or more sulfobetaines and an anionic surface-active detergent and washing the tissue replacement in serial solutions of the buffered salt to remove excess detergent. The natural, cell-free tissue replacement may be a nerve graft that supports axonal regeneration, guides the axons toward the distal nerve end and/or is immunologically tolerated. Other forms of the invention are a composition and kit prepared by the method of making a native, cell-free tissue replacement. The present invention may be modified for use in diagnostic, therapeutic, and prophylactic applications.

26 Claims, 8 Drawing Sheets

(56) References Cited

OTHER PUBLICATIONS

Gulati, A.K., "Evaluation of acellular and cel lar nerve grafts in repair of rat peripheral nerve" (1988) J Neurosurg 68, 117-123.

Gulati, et al. "Nerve graft immunogenicity as a factor determining axonal regeneration in the rat" (Jan. 1990) J Neurosurg 72, 114-122.

Gulati, et al., "Immunogenicity and Regenerative Potential of Acellular Nerve Allografts to Repair Peripheral Nerve in Rats and Rabbits." Acta Neurochir (1994), 126:158-164.

Gulati, et al., "The influence of cultured Schwann cells an regeneration through acellular basal lamina grafts," Brain Research (1995), 705:118-124.

Gulati, A.K., "Immune Response and Neurotrophic Factor Interactions in Peripheral Nerve Transplants" (1998) Acta Haematol 99, 171-174.

Haase, et al., "Peripheral nerve reconstruction using acellular nerve grafts." Surgical Forum (2000), 51:607-608.

Haase, et al., "Recovery of Muscle Contractile Function Following Nerve Gap Rena; with Chemically Accelularized Peripheral Nerve Grafts" Journal of Reconstructive Microsurgery, vol. 19, No. 4, May 2003.

Hall, S.M. "Regeneration in Cellular and Acellular Autografts irr the Peripheral Nervous System" (1986) Neuropathol Appl Neurobiol 12, 27-46.

Hirata, et al. "Differential response of macrophage subpopulation to myelin degradation in the injured rat sciatic nerve" (1999) J Neurocytol 28, 685-695.

Hudson, et al. "Engineering Strategies for Peripheral Nerve Repair" (Jul. 2000) Orthop Olin North Am 31, 485-497.

Hudson, et al., "Engineering an Improved Acellular Nerve Graft via Optimized Chemical Processing," Tissue Engineering, (2004), 10:1346-1353.

Hudson et al., "Optomized Acellular Nerve Graft is Immunologically Tolerated and Supports Regeneration," Tissue Engineering, (2004), 10:1641-1651.

Ide, et al. "Nerve regeneration through allogeneic nerve grafts, with special reference to the role of the Schwann cell basal lamina" (1990) Prog Neurobiol 34, 1.

Ide, et al. "Long Acellular Nerve Transplants for Allogeneic Grafting and the Effects of Baslc Fibroblast Growth Factor on the Growth of Regenerating Axons in Dogs: A Preliminary Report" (1998) Exp Neurol 154, 99.

Jander, et al. "Differential Recruitment of CD8+ Macrophages During Wallerian Degeneration in the Peripheral and Central Nervous System" (2001) Brain Pathol 11, 27-38.

Johnson, et al. "Preparation of Cell-free Extracellular Matrix from Human Peripheral Nerve" (1982) Muscle Nerve 5, 335.

Krekoski, et al. "Axonal regeneration into acellular nerve grafts enhanced by degradation of chondrortin sulfate proteoglycan" (Aug. 15, 2001) J Neurosci 21, 6206-6213.

Llindborg, G. "A 25-year Perspective of Peripheral Nerve Surgery Evolving Neuroscientific Conceptsand Clinical Significance" (2000) J Hand Surg [Am] 25, 391-414.

Martini, R. "Expression and functional roles of neural cell surface molecules and extracellular matrix component: during development and regeneration of peripheral nerves" (1994) J Neuracytol 23, 1-28.

Merriam-Webster Online Dictionary, "Extract" http://www.m-w.com/cgi-bin/dictionary!book=Dictionary&va=extracted, accessed Jul. 5, 2005.

Osawa, et al. "Allogeneic nerve grafts in the rat, with special reference to the role of Schwann cell basal laminae in nerve regeneration" (1990) J Neurocytol 19, 333-849.

Perry, et al. "Macrophages and nernerve regeneration" (1992) Curr Opin Neurobid 2, 679-682.

Pollard, et al. "A Comparison of the Effects of Irradiation and Immunosuppressive Agents on Regeneration through Peripheral Nerve Allografts: An Ultrastructural Study" (1973) Acta Neuropathol (Berl) 23, 166.

Pollard, et al. "An Ultrastructural Comparison of Peripheral Nerve Ailografts and Autografts" (1973) Acta Neuropathol (Berl) 23, 152-165.

Pollard, et al. "Fresh and predegenerate nerve allografts and isografts in trembler mice" (1981) Muscle Nerve 4, 274.

Sigma-Aldrich, "Detergent Product Index: Biological Detergents," http://www.sigmaaldrich.com/Area_of_Interest/Biochemicals/Biological_Detergents/Detergent_Product_Index.html, accessed Jul. 8, 2005.

Sigma-Aldrich, "Detergent Properties and Applications," http://www.sigmaaldrich.com/img/assets/15402/Detergent_Selection_Table.pdf, accessed Jul. 8, 2005.

Sondell, et al "Regeneration of therat sciatic nerve into allografts made acellular through chemical extraction." Brain Res (1998), 795:44-54.

Sondell, ei al., "Vascular Endothelial Growth Factor has Neurotrophic Activity and Stimulates Axonal Outgrowth, Enhancing Cell Survival and Schwarin Cell Proliferation in the Peripheral Nervous System" (1999), 14:5731-5740.

Sorensen, et al. "Axonal elongation through long acellular nerve segments depends on recruitment of phagocytic cells from the near-nerve environment. Electrophysiological and morphological studies in the cat" (2001) Brain Res 903, 185-197.

Stralich, B. "Use of Nerve Conduit in Peripheral Nerve Repair" (Feb. 2000) Hand Clin 16, 123-130.

Zalewski, et ai. "Evaluation of histocompatibility as a factor in the repair of nerve with a frozen nerve allograft" (Apr. 1982) J Neurosurg 56, 550-554.

* cited by examiner

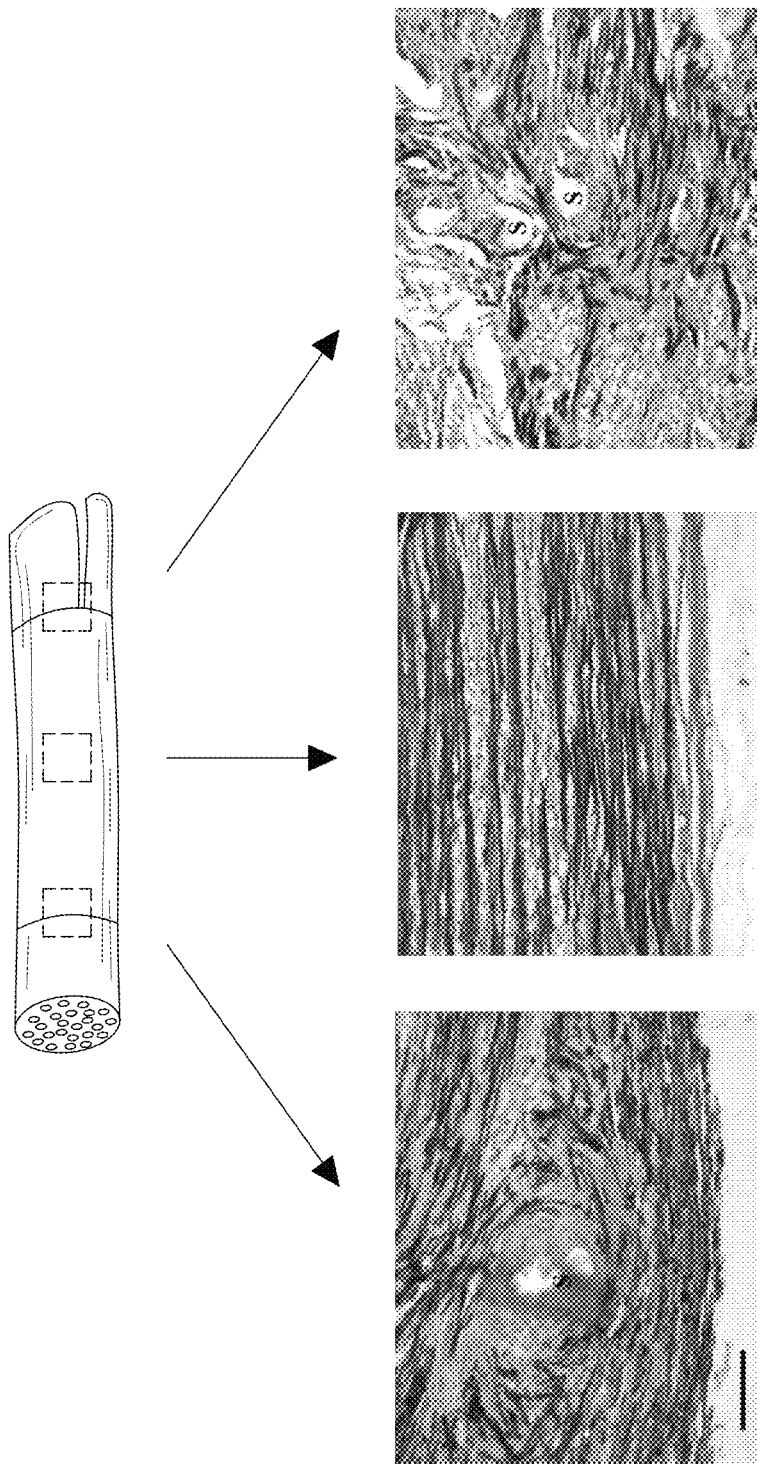

US 9,597,429 B2

CELL-FREE TISSUE REPLACEMENT FOR TISSUE ENGINEERING

CROSS-REFERENCE TO RELATED APPLICATIONS

This application claims priority to and is a continuation of pending U.S. patent application Ser. No. 12/135,772, filed Jun. 9, 2008, now U.S. Pat. No. 8,758,794, issued Jun. 24, 2014, which is a continuation of U.S. patent application Ser. No. 10/672,689, filed Sep. 26, 2003, now U.S. Pat. No. 7,402,319, issued Jul. 22, 2008, which claims priority to U.S. Provisional Patent Application Ser. No. 60/414,278, filed Sep. 27, 2002, the entire contents of all of which are incorporated herein by reference.

STATEMENT OF FEDERALLY FUNDED RESEARCH

The U.S. Government has certain rights in this invention pursuant to the terms of the National Science Foundation Grant No. BES 9733156 and National Institute of Health Training Grant No. 732 GM 08474-09.

BACKGROUND OF THE INVENTION

Tissue engineering faces several challenges in the development of replacement tissue. First, the "replaced" tissue must promote tissue regeneration. In doing so, the replaced tissue must be compatible with the tissue it is replacing so that neighboring cells accept the replacement and do not disrupt tissue continuity. Importantly, the replaced tissue also has to overcome the immunologic challenges faced by any new addition to a biologic system, that of a "foreign body." Furthermore, to be successful, the replaced tissue must eventually exhibit the properties and function of tissue that it is replacing. For example, the replaced tissue should exhibit similar mechanical and structural properties of the native environment or at a minimum, not interfere with the native environment. The replaced tissue may also act as a scaffold to promote cellular regeneration. Finally, the replaced tissue should not stimulate scar formation that limits tissue regeneration or inhibits the natural function of the underlying tissue.

Strategies for successful regeneration include the use of biologic or biocompatible materials to build a bridge across the injured area. While successful for some tissue, many biomaterials have been rejected or have promoted regional "scarring." In addition, the mechanical and structural differences that define the function of different types of tissue have proven difficult to overcome, especially for tissue such as nerves.

These same strategies are modeled on the fabrication of synthetic or biocompatible tissue in vitro that is representative of a native tissue. One example is the use of vascular grafts using an acellular tubular structure that is then implanted at the injured site. The grafts will eventually be invaded by normal cells and the tubular structure will remain viable over time. While promising for tissue with limited needs for mobility, these biocompatible structures are generally stiffer than the surrounding tissue and uncompromising in areas requiring flexibility. Alternatively, biodegradable scaffolds have been engineered with the hope that, over time, the degradable component(s) will be replaced by constituents that make up the normal tissue and will exert the same function as performed by the original tissue. The biodegradable scaffold strategy has seen limited success except to accelerate otherwise naturally occurring phenomena, and have not successfully replaced tissue with high structural or mobility requirements (e.g., bone, nerve, muscle).

For some tissue (e.g. nerve tissue), several other techniques have been used to try to initiate tissue regeneration. For example, acute administration of hydrophilic polymer or polymer blends is used to seal nerve membranes. The polymer application may reconnect or fuse severed axons of damaged nerve membranes and may even promote recovery of excitability in some damaged nerve fibers. However, large injuries are ineffectively repaired using this method, where tension has been found to limit regeneration.

Peripheral nerve allografts have shown some promising success, generally, in the presence of one or more immunosuppressive agents to reduce nerve rejection. The popularity of using nerve conduits for tissue regeneration has increased recently due to the need for alternative tissue reconstruction techniques that yield fewer complications and greater mobility for the individual. In fact, active regenerating fibers on a proximal stump of a nerve have been found to regenerate and progress as a fascicular unit in optimum condition at the trunk of another healthy nerve.

There remains a need to improve tissue replacements, especially for tissue such as nerve that has proven difficult to regenerate with current tissue replacement strategies. The improved tissue replacement should maintain native characteristics of the tissue it is replacing, be able to incorporate bioactive compounds or molecules where necessary to promote rapid regeneration, and stimulate tissue repair and regeneration in the absence of tissue scarring that reduces tissue mobility and integrity. Despite current research efforts in tissue regeneration, there still exists a need for a clinically attractive alternative to autografts.

FIELD OF THE INVENTION

The present invention relates generally to the field of tissue engineering and specifically to the use of cell-free tissue replacements for promoting tissue regeneration.

SUMMARY OF THE INVENTION

The subject matter of the present invention includes a novel method and composition for a replacement tissue that has undergone decellularization while retaining its native structure and integrity. By preserving the structure of the acellular replacement tissue, less remodeling is required by the host after implantation. The present inventors recognized that the native tissue itself serves as the most physiologic environment for tissue regeneration, that is, native tissue appears to be the most viable option for healthy regeneration. To repair a nerve over a gap, e.g., autologous nerve grafts are used herein to physically guide the regenerating axons and to prevent the infiltration of occluding connective tissue. The present invention overcomes several disadvantages of current art, namely, loss of function at the donor site, mismatch of nerve cable dimensions between the donor graft and recipient nerve, and the need for multiple surgeries.

The present invention is a natural replacement tissue or graft not requiring difficult preparation steps with varying temperatures, radiation and/or harsh chemical treatments. The compositions and methods of the invention specifically remove the cellular components without significantly altering the natural extracellular structure. The native extracellular matrix (ECM) structure is preserved (referred to as intact structural components), specifically, the basal laminae and endoneurium/endothelial layer retain their natural and generally original structure. In one embodiment, the invention includes an optimized acellular nerve graft that supports axonal regeneration, guides the axons toward the distal nerve end and is tolerated immunologically. The optimized acellular nerve graft may be, e.g., an isograft, an autograft, an allograft and even a xenograft.

In one form, the present invention is a method for preparing a native, cell-free tissue replacement that includes the steps of; washing the tissue replacement overnight in a solution comprising sulfobetaines, washing tissue replacement in serial solutions of a buffered salt, washing tissue replacement in a mixture of sulfobetaines with an anionic detergent, e.g., TRITON®™ X-200, and washing the tissue replacement in serial solutions of the buffered salt to remove excess detergent.

The present invention is also a native, cell-free tissue replacement, e.g., made using the method of the present invention. In another form, the present invention is a kit for tissue replacement that a cell-free native tissue replacement. The kit may also include one or more solutions useful for re-suspending the cell-free native tissue replacement of the present invention, e.g., a buffered, sterile saline solution that is pharmacologically acceptable as will be know to the skilled artisan. Furthermore, the native, cell-free tissue replacement or graft may also include a vial or solution with cells that may be added to gaps to improve the growth of nerve and other cells, e.g., Schwann cells. The kit may further include an instruction sheet or booklet that provides the user with detailed instructions for the use and procedure for insertion of the native, cell-free tissue replacement. In one embodiment, the native, cell-free tissue replacement forms part of a suture, tube, sheet, film, scaffold, valve, limb replacement, tissue transplant, and joint for delivery into a host.

The present invention is also an optimized acellular graft that supports axonal regeneration, guides the axons toward the distal nerve end and is immunologically tolerated. In one example, the graft is a nerve graft. The acellular graft may also include a cell, a polymer, a bioactive compound or combinations thereof and may be stored at a low temperature, e.g., about 0 to 4 degrees centigrade in a sterile, buffered solution until use. The temperature may be lower or higher depending on the solution in which the graft is stored before use, e.g., including one or more preservative agents. In one embodiment, the acellular graft may also include one or more cells placed in the gap between prior to graft implantation. The graft of the present invention is able to be implanted with reduced T-cell mediated immune response, e.g., CD8+ or CD4+ T cells.

BRIEF DESCRIPTION OF THE DRAWINGS

The above and further advantages of the invention may be better understood by referring to the following description in conjunction with the accompanying figures in which:

FIGS. 8A, 8B and 8C show the Axonal regeneration through acellular nerve grafts was demonstrated by staining longitudinal tissue segments for neurofilaments. The random patterns in the axons at the junctions of the proximal nerve and graft (8A) and the graft and distal nerve (8C) suggest a lack of guidance as the axons crossed into and out of the graft (Scale bar=100 µm);

DETAILED DESCRIPTION OF THE INVENTION

Figure 1:
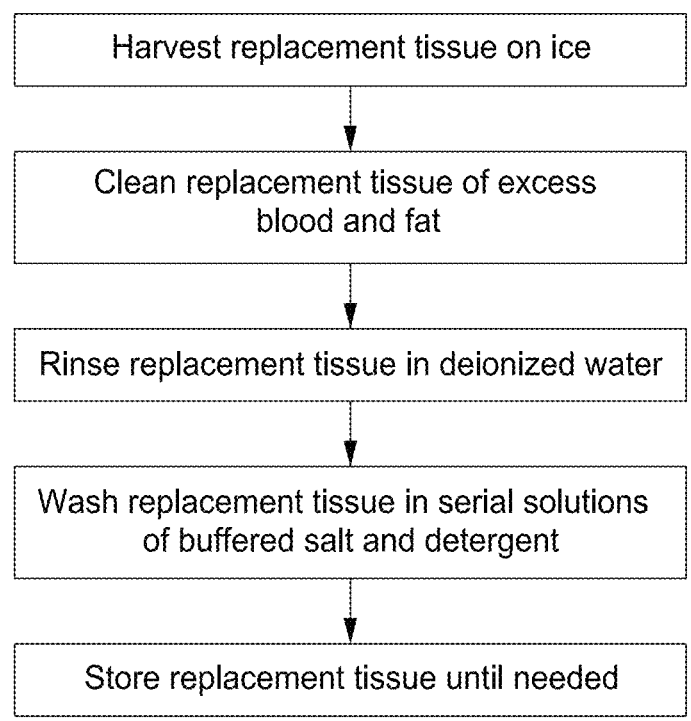
FIG. 1 depicts a flowchart for the preparation of the present invention.

While the making and using of various embodiments of the present invention are discussed herein in terms of a biomaterial for use as a tissue replacement (e.g., peripheral nerve graft, a tissue graft, or implant that can be used to study and stimulate growth and regeneration), a conducting polymer that can used to stimulate cell response, and method for preparing the biomaterial, it should be appreciated that the present invention provides many inventive concepts which can be embodied in a wide variety of specific contexts. The specific embodiments discussed herein are merely illustrative of ways to make and use the invention are not meant to limit the scope of the present invention in any way.

Terms used herein have meanings as commonly understood by a person of ordinary skill in the areas relevant to the present invention. Terms such as "a," "an," and "the" are not intended to refer to only a singular entity, but include the general class of which a specific example may be used for illustration. The terminology herein is used to describe specific embodiments of the invention, but their usage does not limit the invention, except as outlined in the claims. All technical and scientific terms used herein have the same meaning as commonly understood by one of ordinary skill in the art to which this invention belongs, unless defined otherwise. Methods and materials similar or equivalent to those described herein may be used in the practice or testing of the present invention, the generally used methods and materials are now described. The following abbreviations are used herein: extracellular matrix (ECM), sulfobetaine-10 (SB-10), sulfobetaine-16 (SB-16), 3,3' diaminobenzidine (DAB), Harlan Sprague-Dawley (HSD), horseradish peroxidase (HRP), major histocompatibility complex (MHC) and phosphate buffered saline (PBS).

There is currently no effective treatment for damage to central nervous system (CNS) nerves or for absolute tissue regeneration, although drugs can reduce swelling and damage to tissue such as the spinal cord. In contrast to spinal cord injury, there exist therapies, although not optimal, for the treatment of damaged peripheral tissue such as nerves. Current clinical treatments for peripheral nerve injury are surgical end-to-end anastomoses and autologous nerve grafts. Surgical end-to-end repair involves the direct reconnection of individual nerve fascicles and is useful only if nerve ends are directly adjacent, as tension in the nerve cable prohibits regeneration.

A replacement is needed for the autologous graft, the primary clinical treatment of peripheral nerve injuries that involve a defect too large to be repaired by end-to-end reconnection. As described hereinabove, the present inventors have developed an optimized acellular nerve allograft that retains the extracellular structure of peripheral nerve tissue via an improved chemical decellularization treatment. The decellularization process removes cellular membranes from nerve tissue, thus eliminating the antigens responsible for allograft rejection.

The present invention describes the composition and method of a natural-based biomaterial graft developed from native tissue that is free of cells while retaining the intrinsic structure and architecture of the native tissue. As used herein the term "native, cell-free tissue replacement" is used to describe a tissue that has been removed from a host animal (live or cadaveric) that has been treated according to the present invention (also referred to as "acellular grafts"). The term "optimized acellular nerve allograft," as used herein is used to describe a native, nerve cell-free tissue replacement allograft. As used herein, the terms "cell-free," "acellular," "decellular," are used interchangeably and all represent a tissue generally absent of cells, e.g., living cells. The removal or absence of cells will depend on the detergents and conditions used for removal of cells. The level of cell removal will depend on the exact source, methodology and need for the removal of cells. By cell removal a broad range of removal may be used with the present invention, e.g., removal of 70, 80, 90, 95, 99 or about 100 percent of living cells is included. The extent of cell removal reduces the likelihood of a strong immunologic rejection when using a non-autologous tissue source or a source of tissue that is not matched in terms of histocompatibility, e.g., from a donor from the same or even a different species (a xenograft).

The term "acellular graft" as used herein refers to biological material derived from a donor for transplantation into a recipient. The graft is derived from any mammalian source, including human, whether from cadavers or living donors. In some cases it is useful that the source of the graft donor is matched for HLA class I and/or class II antigens with the recipient or host.

The term "mammal" refers to any animal host classified as a mammal, including humans, domestic and farm animals, and zoo, sports, or pet animals, such as dogs, horses, cats, cows, etc. By "compatible" is meant a mammalian host that will accept the donated graft, e.g., a human host. If both the donor of the graft and the host are human, they are preferably matched for HLA class II antigens so as to improve histocompatibility. The present invention, however, serves to overcome problems with problems generally associated with lack of histocompatibility by providing a tissue replacement that does not stimulate the host immune response.

The term "donor" as used herein refers to the mammalian species, dead or alive, from which the graft is derived, e.g. a human donor. Human donors may be volunteers that are blood-related donors that are normal on physical examination and of the same major ABO blood group, because crossing major blood group barriers possibly prejudices survival of the allograft.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, i.e., derived from a human of the same or different genetic origins. The graft, herein referred to as native, cell-free tissue replacement tissue, may be used as a simplified model system with which to study the various stages and critical factors involved in tissue regeneration. In addition, the model native, cell-free tissue replacement tissue may be used for clinical applications.

The replacement tissue is created generally from human cadaver tissue, however, other tissue sources such as from the host or a donor, be it human or other mammal, may be used.

An optimized combination of detergents in a salt and phosphate buffered solution are used in methods of the present invention. The detergents include sulfobetaines with a hydrophilic tail composed of 10 to 16 carbons and TRITON®™ X-200. Detergents used in the present invention are those that specifically rupture cells inside the tissue but do not damage the structural proteins (those that include the extracellular matrix). Cellular debris may be removed using a number of techniques known in the art, such as washing with buffered isotonic solutions and/or physically removing other non-structural debris such as fat. Compared to an allograft, the resulting acellular replacement tissue elicits a significantly reduced immunologic response because surface cell antigens have been removed.

Several uses of the present invention include: 1) as biocompatible biomaterial that is generally non-immunogenic; 2) as a structural foundation for other soluble factors to promote tissue- and host-specific, tissue regeneration; and 3) as a research tool to study the host response to replacement tissue structure. The present invention also includes a replacement tissue that is a native, generally acellular tissue with processible, biologic, bioactive, and/or biodegradable features. Preparation of the present invention and examples are further provided below.

Tissue Replacement Compositions and Delivery. The present invention may be delivered to the body in the form of a modified native, cell-free tissue replacement structure in the form of, e.g., sutures, tubes, sheets, films, valves, joints, vessels, and scaffolds. These modified native, cell-free tissue replacement structures (also referred herein as scaffolds) are thus prepared using the methods taught herein and modified as discussed below. For example, the native, cell-free tissue replacement may be cast using procedures known to those skilled in the art.

While cells are generally removed from the present invention, it may be acceptable and often necessary to reintroduce one or more different type of cells to the present invention. These cells may be obtained direct from a donor, from a culture of cells from a donor, or from cell culture. Donor cells are generally obtained by biopsy and grown to confluence in culture using standard conditions apparent to those of skill in the art. The donor or cells obtained from the donor may be immunosuppressed as needed, for example, using a schedule of steroids and other immunosuppressant drugs, if required. Immunosuppression of the host may provide immunoprotection of cell transplants while a new tissue or tissue equivalent is growing by excluding the host immune system. In addition, the present invention may be used to provide multiple cell types, including genetically altered cells, clones or transplants, within the three-dimensional architecture of the present invention for the purpose of transplant engraftment, immunotherapy, cognitive function, tissue regeneration, repair or reconstruction. Examples of cells include, but are not limited to, chondrocyte, osteoblast, muscle cell, thyroid cell, parathyroid cell, immune cell, pancreatic cell, fibroblast, hepatocyte, epithelial cell, islet cell, nerve cell, and other cells acting primarily to synthesize and secrete or metabolize materials, as well as biopsied or cloned cells of the intestines, kidney, heart, brain, spinal cord, muscle, skeleton, liver, stomach, skin, lung, reproductive system, nervous system, immune system, spleen, bone marrow, lymph nodes, glands.

Alternatively, the present invention may include bioactive molecules formulated with one or more active species so that the present invention becomes a carrier for one or more active species. Whether native or casted, the native, cell-free tissue replacement may also include active agents incorporated into an added polymer or polymer solution (e.g., a polymer scaffold) or may be attached directly to the surface of or within the present invention using techniques readily apparent to those skilled in the art. For example, the active agents may be added by curing on and into the native, cell-free tissue replacement, bonded ionically, covalently and/or using a crosslinking agent, e.g., a cleavable crosslinking agent.

In some instances, it may be useful to incorporate or attach the inactive version of the active agent or species (active agent and species may be used interchangeably) that can then be activated to the active species as needed and required, possibly in a time-released manner, light-activated (e.g., UV) activated in situ by local enzymes or by providing the site with an activating agent exogenously, e.g., providing a patient with an oral activating agent. The active agent may be a drug or other biologically active compound; thus the present invention may be a microcarrier for the delivery of drugs or other biologically active compounds when used in the body. Examples of biologically active compounds are proteins, peptides, polysaccharides, nucleic acids, oligonucleotides, natural and synthetic organic or inorganic molecules, and those biologic molecules used for therapeutic, prophylactic or diagnostic purposes. Drugs may include antibiotics, antivirals, chemotherapeutic agents, immunosuppressive agents, growth factors, anti-angiogenic agents, hormones, anti-inflammatory agents, drugs having an effect on vascular flow, cellular metabolics, or that are effective against one or more diseases and/or combinations thereof.

Other active agents may also be included with the present invention, e.g., non-steroidal anti-inflammatory drugs (NSAIDs) such as propionic acid derivatives; acetic acid derivatives; fenamic acid derivatives; biphenylcarboxylic acid derivatives; and oxicams. Examples of propionic acid derivatives include: ibuprofen, naproxen, ketoprofen, flurbiprofen, fenoprofen, suprofen, fenbufen, and fluprofen may be mentioned as preferred compounds. Acetic acid derivatives derivatives include: tolmetin sodium, zomepirac, sulindac and indomethacin. Fenamic acid derivatives derivatives include: mefenamic acid and meclofenamate sodium. Diflunisal and flufenisal are biphenylcarboxylic acid derivatives, while oxicams include piroxicam, sudoxicam and isoxicam. Other analgesics for use with the present invention include acetominophen and phenacetin. Those skilled in the art will appreciate that any of the foregoing compounds may be used in the form of their pharmaceutically acceptable salt forms, e.g., carboxylic acids with potassium or sodium counter-ions, and the like. The present invention may, therefore, be selectively combined with cells and/or bioactive compounds (e.g., those with active species) to promote tissue/limb reconstruction, tissue regeneration, or tissue/cell/limb transplantation and engraftment. For example, the present invention with cells may be combined with one or more active species such as angiogenic factors, antibiotics, anti-inflammatories, growth factors, alone or in combination with other compounds that induce differentiation and/or cell and tissue growth and regeneration.

Other additives conventionally used in implantable compositions may be included, which are well known in the art. Such additives include, e.g.: anti-adherents (anti-sticking agents, glidants, flow promoters, lubricants) such as talc, magnesium stearate, fumed silica), micronized silica, polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate.

Other additives include, binders (adhesives), i.e., agents that impart cohesive properties to powdered materials through particle-particle bonding, such as matrix binders (dry starch, dry sugars), film binders (PVP, starch paste, celluloses, bentonite and sucrose), and chemical binders (polymeric cellulose derivatives, such as carboxy methyl cellulose, HPC and HPMC; sugar syrups; corn syrup; water soluble polysaccharides such as acacia, tragacanth, guar and alginates; gelatin; gelatin hydrolysate; agar; sucrose; dextrose; and non-cellulosic binders, such as PVP, PEG, vinyl pyrrolidone copolymers, pregelatinized starch, sorbitol, and glucose).

For certain implanted composition that also include active agents it may be useful to provide buffering agents (or bufferants), where the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and where the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid.

In some compositions additives may also include: chelating agents (such as EDTA and EDTA salts); colorants or opaquants (such as titanium dioxide, food dyes, lakes, natural vegetable colorants, iron oxides, silicates, sulfates, magnesium hydroxide and aluminum hydroxide); coolants (e.g., trichloroethane, trichloroethylene, dichloromethane, fluorotrichloromethane); cryoprotectants (such as trehelose, phosphates, citric acid, tartaric acid, gelatin, dextran and mannitol); and diluents or fillers (such as lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose).

It should be appreciated that there is considerable overlap between the above-listed additives in common usage, since a given additive is often classified differently by different practitioners in the field, or is commonly used for any of several different functions. Thus, the above-listed additives should be taken as merely exemplary, and not limiting, of the types of additives that can be included in compositions of the present invention. The amounts of such additives may be readily determined by one skilled in the art, according to the particular properties desired.

One method of the present invention is a native, cell-free tissue replacement (with or without cells) that has been at least partially purified (in a purified or inactive form) in a buffered solution as outlined in the flowchart of FIG. 1. The native, cell-free tissue replacement purified as demonstrated herein may also include one or more active agents may or may not then be trapped within and/or on the invention by a variety of means, including, but not limited to, cross-linking the active agents to the native, cell-free tissue replacement of the present invention. Non-adsorbed or trapped molecules (and or cells) are washed off prior to use. Alternatively, the one or more active agents may be dried directly onto the surface of the present invention or may be cross-linked to, e.g., a polymer or saccharide (with or without cells), that is incorporated onto the surface of or within the present invention.

For example, one or more active and inactive agents factors may be mixed in a slow-release form with a cell-saccharide suspension and allowed to contact and permeate the present invention prior to its implant or transplantation. The saccharide may then be cross-linked to trap the cells within and on the present invention. Alternatively, a polymer solution may be modified to bind the one or more agents or signal recognition sequences prior to its combination with a suspension of cells. In one embodiment of the present invention the agents, active or inactive, may include whole, partially purified or purified proteins, saccharides, lipids and the like from tissue humors, e.g., blood, tissue ascities, peritoneal lavage and the like, as will be known to the skilled artisan.

The native, cell-free tissue replacement of the present invention may also be used for direct implantation and/or injection. When used to repair tissue, promote regeneration, replace damaged cells, enhance growth, proliferation and differentiation or for transplantation, reconstruction, and improved tissue, organ or limb function, the effectiveness of the present invention (including the cells and/or active species components where applicable) can readily be optimized by those skilled in the art without undue experimentation by using the methods described herein.

The present invention may be implanted with materials that include sutures, tubes, sheets, adhesion prevention devices, wound healing products, tissue healing agents and other tissue or cell growth promoters that further enhance the effectiveness of tissue regeneration. In addition, when provided with an electrically conductive material a voltage or current may be applied directly to the present invention at the repair, implant, transplant or reconstruction site. Polymers or other molecules with piezoelectric or electrically conducting properties may also be incorporated into the present invention. Several electroactive polymers exist including piezoelectric (e.g., polyvinylidene fluoride) and electrically conducting materials (e.g., polypyrrole (PP), and polythiophene). Since piezoelectric materials depend on small mechanical deformations to produce transient surface charges, the level and duration of focused stimulation cannot be controlled. In contrast, electrically conducting polymers readily permit external control over both the level and duration of stimulation. Thus, strategies designed to enhance the regeneration of a responsive cell might employ electrically conducting polymers. For diagnostic purposes, the present invention may be incorporated not only with molecules containing active species but also with one or more detectable agents or molecules that allows for the diagnosis, monitoring and/or prophylactic measures. Examples of suitable detectable agents include dyes, labels, metals, detection devices, and electronic chips.

Thus, the methods used to prepare the present invention and the composition of the present invention serve several beneficial functions when used in mammals, including regenerative, restorative, reconstructive, therapeutic, prophylactic, and diagnostic functions. Applications include its use as a graft, implant, scaffold, limb replacement, in transplantation, muscle or tissue resection, and as a tube, sheet, film, vessel or nerve.

Example 1

Preparation of Native Cell-free Tissue. Solutions used for the preparation of native, acellular nerve tissue include, e.g., RPMI medium, double distilled water (ddH2O), 100 mM Na/50 mM phosphate buffered solution, 50 mM Na/10 mM phosphate buffered solution, SB-10 (5×CMC) in 50 mM Na/10 mM phosphate buffered buffer solution, an anionic surface-active detergent (such as TRITON®™ X-200/SB-16 [0.07%/5×CMC] in 50 mM Na/10 mM phosphate buffered solution). All solutions were either filter sterilized or autoclaved as appropriate for the preparation of samples to be used in a sterile field; techniques of which are readily apparent to those of skill in the art. Examples of anionic surface-active detergents that may be used and adapted with the method of the present invention include, e.g., TRITON®™ X-200, TRITON®™ W-30 Conc., TRITON®™ GR-5M, TRITON®™ GR-7M, TRITON®™ DF-20, and TRITON®™ QS-44.

In advance of retrieving the tissue, sterile RPMI medium is added to, e.g., a 15 mL conical tube and kept on ice. The sciatic nerve tissue from a donor animal is generally harvested using sterile techniques. Harvested tissue is immediately placed in cold RPMI medium, preferably under a flow hood or in a sterile environment (e.g., operating room), and return tube to ice. Tissue is then arranged for viewing under a dissecting microscope in the laminar flow hood, preferably wiped down in advance with a sterile solution such as 70% ethanol. A dissecting microscope may not be necessary for larger tissue that is readily viewed by eye. It will generally be useful to clean the fat, excess blood and other tissue or tissue debris from the tissue to be implanted in a sterile environment and while in a nutrient media. Nerve tissue, for example, may be placed in a sterile Petri dish filled with nutrient medium such as RPMI. Nerve is best viewed under the microscope to remove excess fat and connective tissue.

After cleaning the tissue, tissue is placed in a sterile tube containing $ddH_2O$. Again, to maintain sterility, all remaining steps should generally be performed in a sterile environment such as a laminar flow hood, clean room or other similar sterile field. Tissue is rinsed in $ddH_2O$ for about 7 hours with several changes of solution. Solutions may be removed after each change using a sterile-tipped vacuum aspirator, where the tissue is first centrifuged to keep it at the bottom of the tube. Several additional washing solutions follow, including: SB-10 solution, solution overnight; three times in 100 mM Na/50 mM phosphate buffered solution, washes should be about 15 minutes each; TRITON®™ X-200/SB-16 solution for about 24 hours; three times in 100 mM Na/50 mM phosphate buffered solution, washes should be about 15 minutes each; SB-10 solution for about 7 hours; three times in 100 mM Na/50 mM phosphate buffered solution, washes should be about 15 minutes each; TRITON®™ X-200/SB-16 solution, overnight; three times in 100 mM Na/50 mM phosphate buffered solution, washes should be about 15 minutes each. Tissue can then be stored at a low temperature, e.g., about 4 degrees Centigrade (4° C.) in 50 mM Na/10 mM phosphate buffered solution until use. The compositions and methods disclosed herein allow for the use of other detergent combinations for the removal of cells without creating structural damage (thereby retaining extracellular matrix and essential components), as will be recognized by the skilled artisan. Detergents and conditions for the use of the detergents, buffers and ionic conditions that mimic those disclosed herein may be used by the skilled artisan and are encompassed by the present invention.

Immune Response of Native Cell-free Tissue. The immune response of tissue prepared with the method of the present invention show that the native cell-free tissue adapts to its environment and is not rejected. Furthermore, the composition of the present invention (the native cell-free tissue) is not rejected as other tissue replacements or allografts typically are. Examples of this are presented in more detail below.

Native-cell free tissues were evaluated for their immune response following implantation as a cell-free sciatic nerve graft. Four conditions were evaluated and include:
1. Fresh isografts (i.e., not treated with methods of the present invention) removed/harvested from three Lewis rats (i.e., the donors) and implanted, one each, into three Lewis rats (i.e., the hosts);
2. Fresh allografts (i.e., not treated with methods of the present invention) removed/harvested from five Lewis rats (i.e., the donors) and implanted, one each, into five Harlan Sprague Dawley rats (i.e., the hosts);
3. Cell-free native tissue allografts (i.e., treated with the methods of the present invention) removed/harvested from five Lewis rats (i.e., the donors) and implanted, one each, into five Harlan Sprague Dawley rats (i.e., the hosts); and
4. Cell-free native tissue isografts (i.e., treated with the methods of the present invention) removed/harvested from three Sprague Dawley rats (i.e., the donors) and implanted, one each, into three Harlan Sprague Dawley rats (i.e., the hosts).

Conditions 2 and 4 were used specifically because Lewis and Harlan Sprague Dawley rats express different RT1 halotypes, and, in general, are found to reject tissue that is not from the same species (i.e., Harlan Sprague Dawley reject tissue from Lewis rats and vice versa). The same-strain, fresh isograft implant (condition 1) was used to examine the immune response resulting from implantation of a graft containing viable cells. This condition is largely compatible with the current clinical approach (the autograft) used for several types of tissue repair, such as nerve tissue repair. The cross-strain, fresh allograft implant (condition 2) was used as a typical positive rejection immune response. Condition 3 or the cross-strain, cell-free native tissue allografts were used to determine if immunologic rejection occurred after using a composition and method of the present invention. And condition 4 using the same-strain cell-free native tissue isograft was designed to evaluate immunologic responses after surgery employing the composition and methods of the present invention.

Observed immune responses that were followed were CD8+ invasion and macrophage invasion. Macrophages are immune cells that are released in response to injury and believed to be one cell responsible for clearing the debris that occurs at and near the site of injury. It is believed that when foreign bodies are introduced at the site of injury, such as during tissue replacement or grafting, macrophages will invade the site in even higher numbers and are, thus, involved in clearing the site of all foreign bodies, including the graft. This is especially true when a graft is rejected.

Rat T-cytotoxic lymphocytes are CD8+ cells, and are also used as indicators of foreign body rejection, including graft or implant rejection. A subset of CD8+ cells are found at a site of injury (e.g., after sciatic nerve injuries), even in the absence of immunologic rejection. Therefore, macrophages and some CD8+ cells are generally present after an implantation, tissue replacement, transplantation or grafting procedure. On the other hand, a significant increase in CD8+ cells in the absence of a large number of macrophages generally indicates rejection of the implant, replacement, transplant, or graft.

All grafts were implanted in the right sciatic nerve of male rats at least about 350 g in weight. Rats were allowed to recover for 28 days and then anesthetized to expose the implanted grafts. Following fixation of each graft from each rat, grafts were extracted, embedded in paraffin, sectioned, sections attached to glass slides, and stained for invading CD8+ and macrophage cells. Methods used for graft fixation, extraction, paraffin embedding, and sectioning are those readily apparent to one of ordinary skill in the art of tissue preparation and histology.

Tissue sections were stained for the presence of macrophages and CD8+ cells. Sections were viewed under a microscope, and several images of each section were captured with a digital camera. Using image analysis software, the percentage of graft tissue that was positively stained for either macrophages or CD8+ cells was determined.

Figure 2:
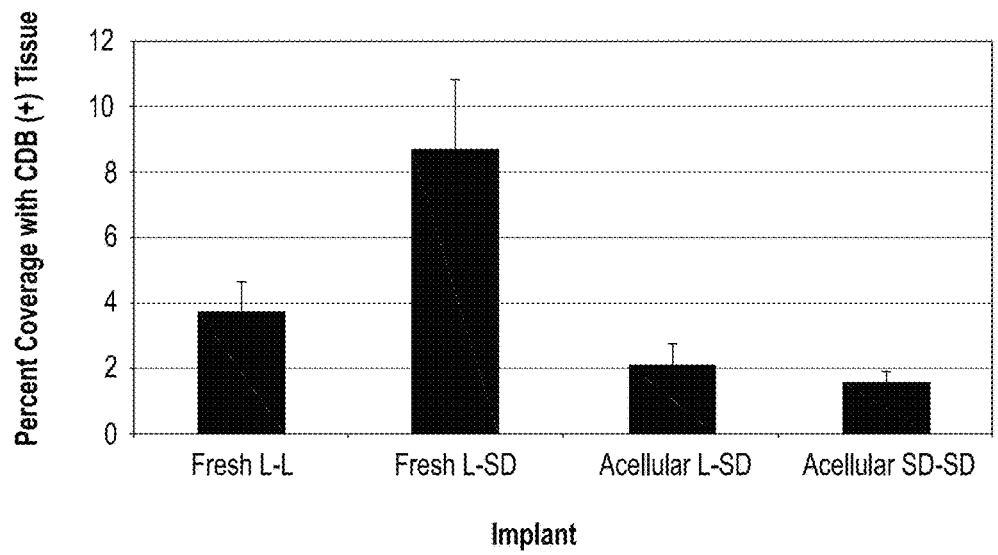
FIG. 2 is a graph that summarizes a tissue immune response with CD8+ invasion in accordance with the present invention.
Figure 3:
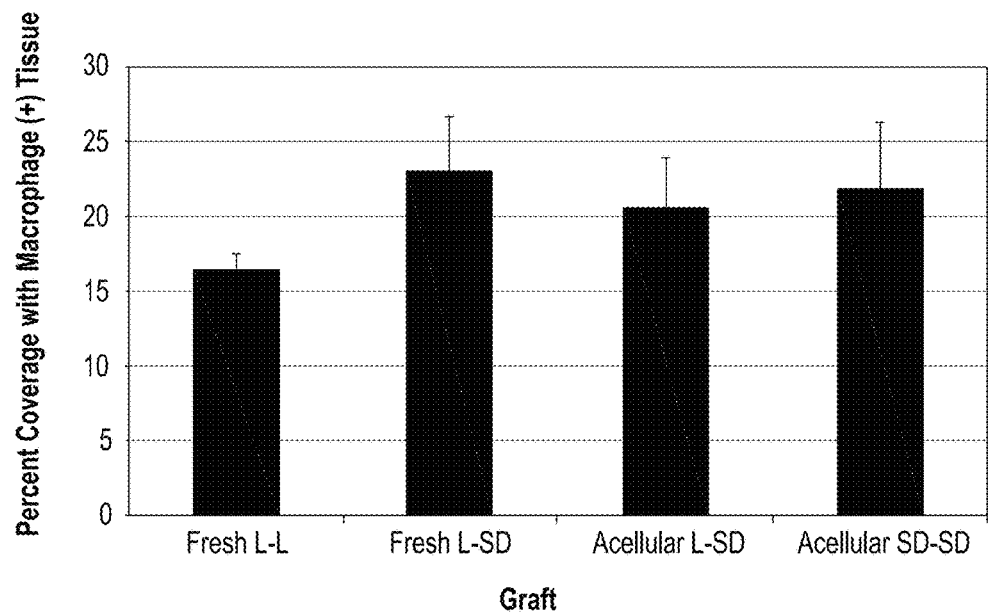
FIG. 3 is a graph showing the tissue immune response with macrophage invasion in accordance with the present invention.
Figure 4A:
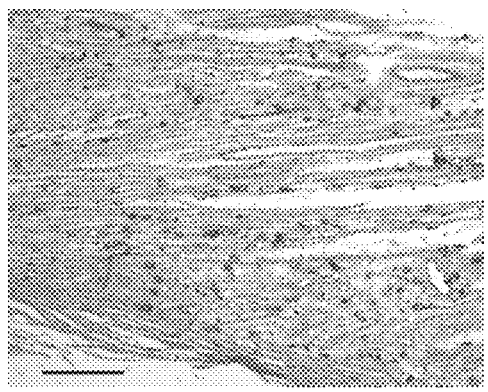
FIGS. 4A, 4B, 4C and 4D are longitudinal sections of tissue that were cut from (4A) fresh isografts, (4B) fresh allografts, (4C) optimized acellular isografts, and (4D) optimized acellular allografts that were harvested 28 days after implantation (Scale bar=200 µm)
Figure 4B:
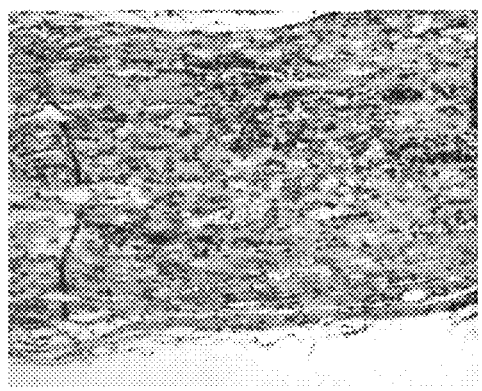
Figure 4C:
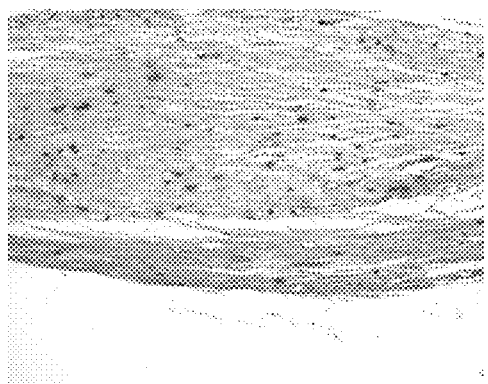
Figure 4D:
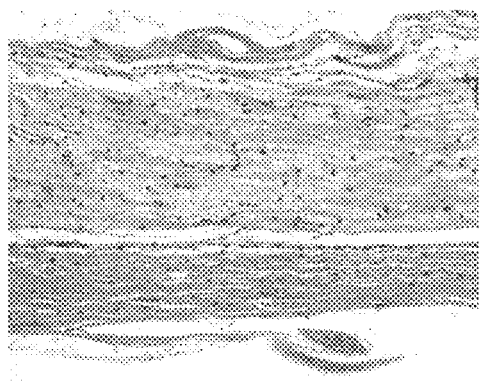

FIG. 2 is a graph that shows the percentage of CD8+ cells that were present after independent grafting using each of the four conditions. FIG. 3 is a graph that shows the percentage of macrophage cells that were present after independent grafting using each of the four conditions. The CD8+ cell invasion results shows that the cross-strain, fresh allograft (condition 2) is undergoing rejection. The levels of CD8+ cells in the cell-free native tissue grafts (conditions 3 and 4) is lower than that observed with the same-strain, fresh isograft (condition 1). Therefore, the cell-free native tissue grafts are not eliciting an increased T-cytotoxic lymphocyte invasion, and thus, not undergoing immunologic rejection.

Macrophage invasion into the cross-strain, fresh allograft (condition 2) was the highest, as would be expected for a graft undergoing rejection. The two cell-free native tissue grafts (conditions 3 and 4) showed lower macrophage invasion than the cross-strain, fresh allograft (condition 2), but both were higher than the same-strain, fresh graft (condition 1), and indicates that an immune response is occurring the cell-free tissue; however the immunologic response is not considered to be a rejection, as is evident from the CD8+ stain. The increased level of macrophages could be the result of several factors, including the more open structure of the cell-free native tissue grafts, compared to the mass transfer inhibiting compact nature of fresh grafts.

The most important finding is that the level of CD8+ cells in the two cell-free native tissue grafts (conditions 3 and 4) is on the same order as that seen in the fresh isografts (condition 1), despite the increase in macrophage levels. Thus, the cell-free native tissue grafts are not undergoing immunological rejection.

cal response of nerve tissue transplants. To test the immunogenicity of the acellular grafts, nerve tissue from Harlan Sprague-Dawley rats was decellularized and implanted into Lewis rats for 28 days. Histological examination of the levels of CD8+ cells and macrophages that infiltrated the acellular grafts suggested that the decellularization process averted cell-mediated rejection of the grafts. In a subsequent experiment, regeneration in the optimized grafts after 28 and 84 days was compared to that in fresh isografts and two published acellular graft models. It was found that using the present invention, the average axon density at the midpoint of the optimized graft was statistically indistinguishable from that in the fresh isograft at both time points, 96% and 910% higher than in the thermally decellularized model described by Gulati (1988), and 42% and 401% higher than in the chemically decellularized model described by Sondell et al. (1998). Using the present invention, the optimized acellular grafts were immunologically tolerated by the removal of cellular material and preservation of the ECM

TABLE 1

|   | Sect. 1 + Area | Sect. 2 + Area | Sect. 3 + Area | Sect. 4 + Area | Sect. 5 + Area | Avg. Area | % Coverage | Avg. % Coverage | Std Dev |
|---|---|---|---|---|---|---|---|---|---|
|   | | | | Condition 1 | | | | 3.671 | 0.922 |
| 1 | 8.37 | 6.86 | 10.26 | 12.18 | 10.51 | 9.636 | 3.778824 | | |
| 2 | 11.46 | 12.36 | 10.88 | 13.42 | 9.7 | 11.564 | 4.534902 | | |
| 3 | 5.6 | 5.32 | 9.06 | 4.78 | 9.67 | 6.886 | 2.700392 | | |
|   | | | | Condition 2 | | | | 8.703 | 2.133 |
| 4 | 23.39 | 21.78 | 22.05 | 25.12 | 22.79 | 23.026 | 9.029804 | | |
| 5 | 19.76 | 21.05 | 23.69 | 28.14 | 20.1 | 22.548 | 8.842353 | | |
| 9 | 34.84 | 22.45 | 25.2 | 29.17 | 40.48 | 30.428 | 11.93255 | | |
| 12 | 14.8 | 17.61 | 15.3 | 15.02 | 16.5 | 15.846 | 6.214118 | | |
| 15 | 22.45 | 18.21 | 17 | 19.25 | 18.67 | 19.116 | 7.496471 | | |
|   | | | | Condition 3 | | | | 2.091 | 0.657 |
| 6 | 4.23 | 3.98 | 5.26 | 4.79 | 4.52 | 4.556 | 1.786667 | | |
| 7 | 6.11 | 5.31 | 5.29 | 4.11 | 5.61 | 5.286 | 2.072941 | | |
| 8 | 4.46 | 4.93 | 5.32 | 5.49 | 4.62 | 4.964 | 1.946667 | | |
| 11 | 6.72 | 9.59 | 8.07 | 10.39 | 5.91 | 8.136 | 3.190588 | | |
| 14 | 3.12 | 3.65 | 3.58 | 3.77 | 4.44 | 3.712 | 1.455686 | | |
|   | | | | Condition 4 | | | | 1.574 | 0.331 |
| 13 | 2.35 | 3.74 | 3.3 | 3.48 | 3.3 | 3.234 | 1.268235 | | |
| 16 | 3.9 | 4.3 | 4.12 | 2.68 | 4.48 | 3.896 | 1.527843 | | |
| 17 | 4.47 | 6.06 | 3.65 | 4.74 | 5.64 | 4.912 | 1.926275 | | |

Abbreviations are:
Sect. = section;
Avg. = average;
+ = positively stained;
Std Dev = standard deviation.

Applications of the present invention include the treatment of injuries (surgical or non-surgical and spinal cord or non-spinal cord injuries), in plastic and reconstructive surgery, for transplantation or as implants, especially in difficult tissue such as peripheral nerve tissue.

Example 2

Replacement Nerve Tissue Graft. A replacement is needed for the autologous graft, the primary clinical treatment of peripheral nerve injuries that involve a defect too large to be repaired by end-to-end reconnection. As described hereinabove, the present inventors have developed an optimized acellular nerve allograft that retains the extracellular structure of peripheral nerve tissue via an improved chemical decellularization treatment. The decellularization process removes cellular membranes from nerve tissue, thus eliminating the antigens responsible for allograft rejection.

In this example, the optimized acellular grafts were tested in vivo for their immunogenicity and regenerative capacity using a well-established rat model system for immunologiaccomplished with the decellularization process described hereinabove and are both beneficial for promoting regeneration through an acellular nerve graft.

Materials and Methods: Creation of Grafts. To create the optimized acellular grafts, both the left and right sciatic nerves were harvested under aseptic conditions from 350 g Harlan Sprague-Dawley (HSD) male rats. All chemicals were purchased from Sigma (St. Louis, Mo.) unless otherwise noted. All solutions were autoclaved or filter sterilized prior to use. The tissue was handled only by the ends to minimize structural damage. When harvested the nerves were immediately placed in RPMI 1640 solution at 4° C. All subsequent steps were conducted in a laminar flow hood for sterility. Fatty and connective tissue were removed from the nerve epineurium. The nerve tissue was cut into 15 mm segments and placed in a 15 ml conical tube filled with deionized distilled water. All washing steps were carried out at 25° C. with agitation. After 7 hours, the water was aspirated and replaced by a solution containing 125 mM sulfobetaine-10 (SB-10), 10 mM phosphate, and 50 mM sodium. The nerves were agitated for 15 hours. The tissue was then rinsed once for 15 minutes in a washing solution of 50 mM phosphate and 100 mM sodium. Next, the washing solution was replaced by a solution containing 0.14% TRITON®™ X-200, 0.6 mM sulfobetaine-16 (SB-16), 10 mM phosphate, and 50 mM sodium. After agitating for 24 hours, the tissue was rinsed with the washing solution 3 times at 5 minutes per rinse. The nerve segments were again agitated in the SB-10 solution (7 hours), washed once, and agitated in the SB-16/TRITON®™ X-200 solution (15 hours). Finally, the tissue segments were washed 3 times for 15 minutes in a solution containing 10 mM phosphate and 50 mM sodium, then stored in the same solution at 4° C.

Acellular nerve grafts were also created according to previously established methods as a basis for comparison. The chemically decellularized model was created by a protocol published by Sondell, et al. Briefly, the nerve tissue was agitated in distilled water for 7 hours, 46 mM TRITON®™ X-100 in distilled water overnight, and then 96 mM sodium deoxycholate in distilled water for 24 hours. These steps were repeated before performing a final wash in distilled water. All treatment steps were performed at room temperature and the tissue was subsequently stored in a 10 mM phosphate buffered saline (PBS) solution at 4° C.

The thermally decellularized model (i.e., a freeze/thaw graft) was created according to the protocol described by Gulati, et al. Immediately after harvest, the nerve tissue was dipped in liquid nitrogen for 20 seconds, thawed in PBS at room temperature for 60 seconds, and then the process was repeated four additional times. The grafts were placed in PBS at room temperature and used within 30 minutes.

Implantation of Grafts. Isografts and allografts were used to study the immunogenicity of the optimized acellular grafts. Isografts were harvested from a donor animal (e.g., Lewis rat) of the same strain as the host animal (e.g., Lewis rat); they mimic the autograft. The autografts served as a negative control, as the immune response would only be due to the surgical procedure. Allografts were harvested from a donor animal (e.g., HSD rat) of a different strain than the host animal (e.g., Lewis rat). The fresh allograft served as a positive control since it elicits a cell-mediated rejection. The acellular isograft was used to examine the in vivo response to the treatment protocol (e.g., the response to residual chemicals).

Table 2 summarizes the test conditions and controls for immunological tolerance determined. The optimized acellular graft was inspected for residual antigens by implanting an acellular allograft. In summary, a total of four conditions studied were tested: (a) fresh isografts (n=6) (b) fresh allografts (n=5); (c) optimized acellular isografts (n=5); and (d) optimized acellular allografts (n=5) (Table 2).

TABLE 2

Implants to Examine Immunological Tolerance of Optimized Grafts

| Graft Type | Donor Strain | Host Strain | Number of Implants | Analyzing Response to: |
|---|---|---|---|---|
| Fresh Isograft | Lewis* HSD† | Lewis HSD | 3 3 | Surgical procedure (negative control) |
| Fresh Allograft | Lewis | HSD | 5 | Natural antigens (positive control) |

TABLE 2-continued

Implants to Examine Immunological Tolerance of Optimized Grafts

| Graft Type | Donor Strain | Host Strain | Number of Implants | Analyzing Response to: |
|---|---|---|---|---|
| Acellular Isograft | HSD | HSD | 5 | Treatment protocol |
| Acellular Allograft | Lewis | HSD | 5 | Residual antigens |

*Lewis rats are an inbred strain (i.e., greater than 98% genetic homogeneity)
†HSD rats are an outbred strain, but the animals used were from a closed colony.

Each rat was anesthetized with an intra-peritoneal injection of 120 mg/kg body weight ketamine (Webster Veterinary Supply, Sterling, Mass.) and 15 mg/kg body weight xylazine (Webster Veterinary Supply). The sciatic nerve on the right side was exposed, transected, and 5 mm of nerve was removed. The ends of the graft were trimmed immediately prior to implantation to attain a clean-cut, 10 mm graft. The graft was sutured to both the proximal and distal nerve ends using 10-0 vicryl sutures (Ethicon, Somerville, N.J.). The muscle was drawn back together with 5-0 chromic gut sutures (Ethicon), and the skin was closed with wound clips (Becton Dickinson, Sparks, Md.). Surgical methods were in accordance with regulations established by the National Research Council in the Guide for the Care and Use of Laboratory Animals.

Immunogenicity of Grafts Evaluated with Histology. The grafts were harvested 28 days after implantation. Each animal was re-anesthetized, and the nerve graft was exposed. Prior to harvesting, the graft was fixed for 1 minute with 3% glutaraldehyde/4% paraformaldehyde in phosphate buffered saline (PBS). Then, the sciatic nerve was transected 5 mm above and below the graft, the distal end was marked with a stitch, and the graft was placed in fixative at 4° C. After 30 minutes, the graft was transferred to PBS and stored at 4° C. until it was embedded in paraffin.

Histology was used to inspect the allografts for signs of immunological rejection. The tissue was dehydrated with graded alcohol solutions and xylene, and then embedded in paraffin. Longitudinal sections of tissue 7 μm thick were cut with a microtome and captured on glass slides. Immunostaining was performed with anti-CD8a+ (Pharmingen, San Diego, Calif.) and anti-macrophage (Chemicon, Temecula, Calif.) primary antibodies. Horseradish peroxidase (HRP) tagged secondary antibodies, 3,3' diaminobenzidine (DAB) substrate (Vector Labs, Burlingame, Calif.), and an eosin counterstain were used to visualize the invading cells. The stained sections were visualized on an Olympus IX70 (Melville, N.Y.) inverted microscope, and the images were captured with an Optronics MagnaFire (Goleta, Calif.) digital color camera. After capturing images of the stained tissue sections, the images were combined in Adobe Photoshop to create a composite of the entire graft. Using Scion Image software (Scion Corporation, Frederick, Mass.), the percentage of area of the graft covered with positively stained CD8+ and macrophage cells was determined.

Acellular Graft Models Compared In Vivo. To study the impact of cellular debris and structural preservation on regeneration, three acellular graft models were examined in vivo. Optimized acellular grafts, grafts created with the Sondell protocol, and freeze/thaw grafts were created as described in the Materials and Methods section. Fresh grafts were also included in the experiments as a positive control. Fresh isografts are a mimic of the clinical autograft. The optimized acellular grafts and Sondell grafts were prepared within 30 days of implantation. The time between harvest and implantation of the freeze/thaw grafts and fresh grafts was never longer than 30 minutes. Donor and host animals were HSD rats.

Histological Comparison of Decellularized Tissues. A comparison of the ECM structure in the acellular grafts prior to implantation was conducted by visualizing the basal laminae. The grafts were prepared as previously described, but were never surgically implanted or fixed. The grafts were embedded and cross-sectioned. An anti-laminin primary antibody (Developmental Studies Hybridoma Bank, Iowa City, Iowa) and a TRITC-conjugated goat anti-mouse secondary antibody (Jackson ImmunoResearch, West Grove, Pa.) were employed in the immunostaining procedure.

Regenerative Capacity of Grafts Evaluated with Histology. As summarized in Table 3, animals with each of the four grafts used in the acellular model comparison were harvested 28 days after implantation. The remaining animals were used to evaluate regeneration after 84 days. Prior to the 84-day time point, however, seven animals were put down due to automutilation of their toes (n=1 fresh graft, n=2 freeze/thaw grafts, n=1 Sondell grafts, n=3 optimized acellular grafts). To evaluate the regenerative potential of the three acellular graft models, longitudinal tissue sections were stained for regenerated axons using an anti-neurofilament primary antibody called RT97 (Developmental Studies Hybridoma Bank), an HRP-conjugated secondary antibody, and DAB. Subsequently, cross sections were cut from the midpoint of the grafts and stained for neurofilaments. The stained sections were visualized with a 20× objective and images were captured with the digital camera. A 20 cm×16 cm image was printed for each sample. The number of nerve fibers in each image was counted, and the area of nerve cable in the image was measured. Because a portion of the nerve cable had been removed by sectioning the tissue longitudinally prior to taking cross-sections, the total number of axons in each nerve cable could not be determined. Instead, axon density was calculated by dividing the number of nerve fibers by the area of the cable from which the count was taken. Select specimens were not used in the axon density analysis because less than 33% of the nerve cable remained after the sample was sectioned longitudinally. The number of samples analyzed for each graft and time point is reported with the axon density data. Regions of connective tissue at the periphery of the graft, based on morphological evaluation, were excluded from the analysis.

Using the present invention the native, cell-free tissue replacement grafts were immunologically tolerated. To evaluate the immunological response by a host to the optimized acellular grafts, four experimental conditions were tested with sciatic nerve graft implants (Table 2). A fresh isograft was used to establish the inflammatory and immune response that results from surgery alone. This served to mimic the current clinical approach (i.e., autograft) for nerve repair (positive control). The fresh allograft established the cellular response associated with cell-mediated rejection (negative control). The acellular allografts were used to determine if there was a reduction or avoidance of immunological rejection by decellularizing the grafts. Finally, acellular isografts were used to determine the immune response that resulted from the processing technique and any residual chemicals remaining in the graft after decellularization.

Figure 7:
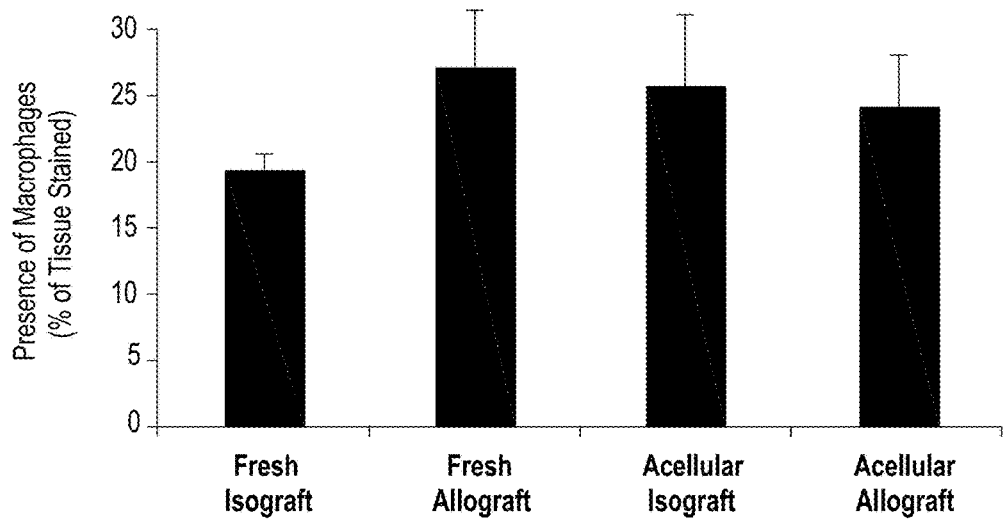
FIG. 7 is a graph that summarizes the level of macrophages present in fresh and acellular nerve grafts after 28 days was evaluated by determining the percentage of area stained in longitudinal tissue sections.
Figure 6A:
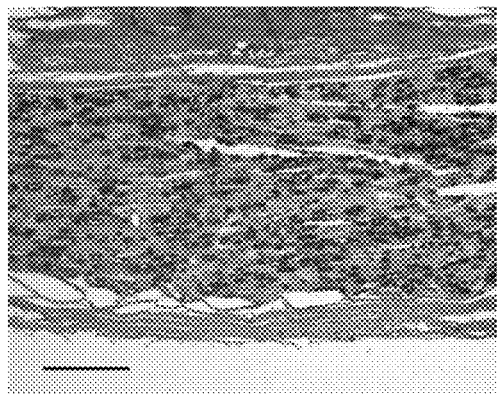
FIGS. 6A, 6B, 6C and 6D are longitudinal sections of tissue were cut from (6A) fresh isografts, (6B) fresh allografts, (6C) optimized acellular isografts, and (6D) optimized acellular allografts that were harvested 28 days after implantation (Scale bar=200 µm)
Figure 6B:
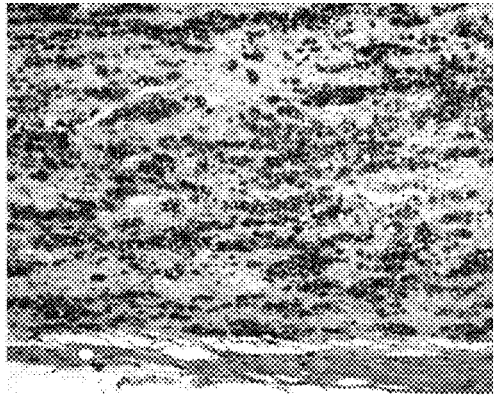
Figure 6C:
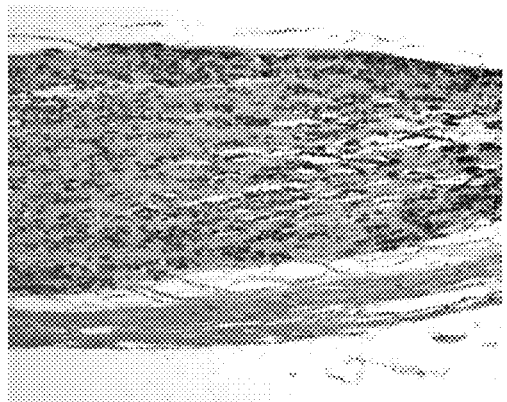
Figure 6D:
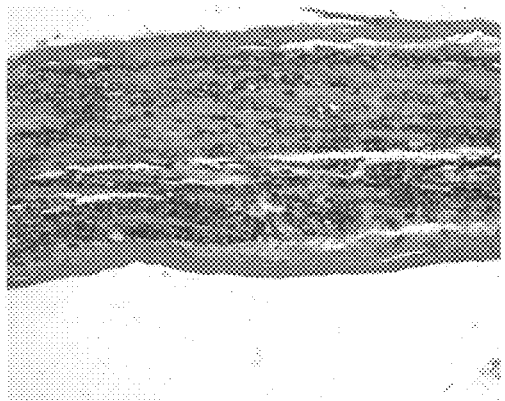

By staining longitudinal sections of the grafts for cytotoxic T-cells and macrophages, the level of cell-mediated immune response was determined. CD8+ cytotoxic T-cells were visualized by staining for CD8 cell surface markers. Elevated levels of cytotoxic T-cells are expected in tissues undergoing cell-mediated rejection. Increased levels of macrophage cells are also expected in rejected allografts. However, macrophages are also recruited during Wallerian degeneration to clear debris and release neurotrophic factors for regenerating nerves. At 28 days, both cell types could be seen throughout the full length of all the grafts (FIGS. 4, 7).

FIGS. 4A, 4B, 4C and 4D are longitudinal sections of tissue that were cut from (4A) fresh isografts, (4B) fresh allografts, (4C) optimized acellular isografts, and (4D) optimized acellular allografts that were harvested 28 days after implantation. The tissue sections were stained for CD8, a surface marker on cytotoxic T-cells. The level of staining in the fresh allografts was visibly higher, but the optimized acellular grafts appeared indistinguishable from the fresh isografts. Scale bar=200 μm.

Figure 5:
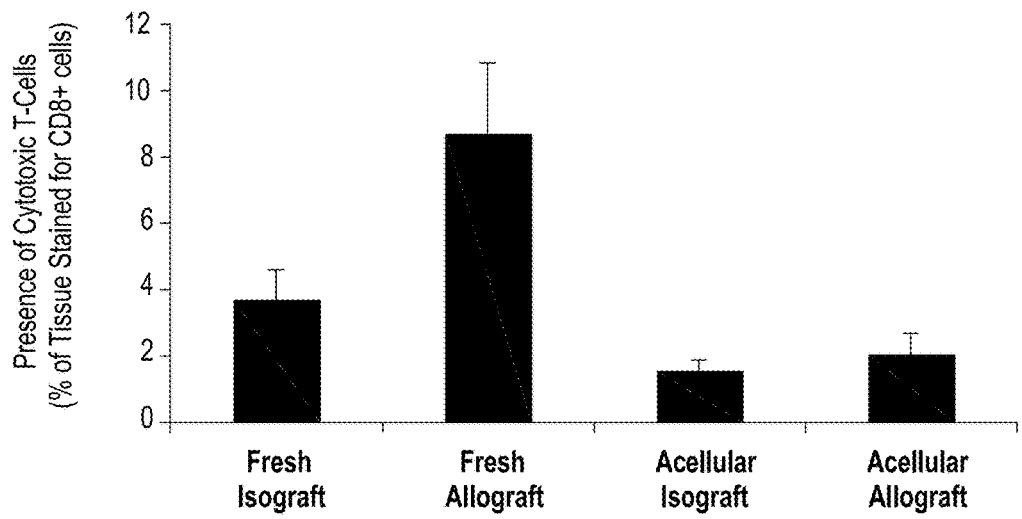
FIG. 5 is a graph that summarizes the cell-mediated immune response in the fresh and acellular nerve grafts was evaluated by determining the percentage of tissue covered by CD8+ cells.

FIG. 5 is a graph that summarizes the cell-mediated immune response in the fresh and acellular nerve grafts was evaluated by determining the percentage of tissue covered by CD8+ cells. The infiltration of CD8+ cells into the fresh allografts was higher than into the fresh isografts ($p<0.01$) and the acellular grafts ($p<0.005$). Fresh allografts demonstrated a statistically significant elevation in CD8+ cells. The optimized acellular isografts and allografts were statistically indistinguishable from the fresh isografts, indicating that

TABLE 3

Implants to Evaluate the Regenerative Capacity of Optimized Grafts

| Graft Type | Total Implants | Put Down Early | Harvested (28 days) | Harvested (84 days) | Usable Cross-Sections (28 days) | Usable Cross-Sections (84 days) | Unusable Cross-Sections (28 days) | Unusable Cross-Sections (84 days) |
|---|---|---|---|---|---|---|---|---|
| Fresh | 15 | 0 | 9 | 6 | 8 | 5 | 1 | 1 |
| Sondell | 11 | 0 | 6 | 5 | 6 | 3 | 0 | 2 |
| Freeze/Thaw | 10 | 0 | 6 | 4 | 6 | 3 | 0 | 1 |
| Optimized Acellular | 18 | 3 | 9 | 6 | 7 | 5 | 2 | 1 |

Statistical Analysis. The Student's t-Test was performed to determine the statistical significance of the differences between results. A significance level of $p<0.05$ was used as the cutoff (i.e., p values are reported only for cases in which $p<0.05$).

after 28 days, cell-mediated immune rejection was only occurring in the fresh allografts.

FIGS. 6A, 6B, 6C and 6D are longitudinal sections of tissue were cut from (6A) fresh isografts, (6B) fresh allografts, (6C) optimized acellular isografts and (6D) optimized acellular allografts that were harvested 28 days after implantation. The tissue sections were stained for macrophages, immune cells involved in Wallerian degeneration, nerve regeneration, and tissue inflammation. Scale bar=200 µm.

Meanwhile, the levels of CD8+ cells in the acellular isografts and allografts were lower than those observed in the fresh isografts (p<0.05). Macrophage invasion into the fresh isografts was lower than into the fresh allografts (p<0.05), but the differences between other grafts were not statistically significant.

FIG. 7 is a graph that summarizes the level of macrophages present in fresh and acellular nerve grafts after 28 days was evaluated by determining the percentage of area stained in longitudinal tissue sections. Fresh allografts demonstrated a statistically significant elevation in macrophages compared to fresh isografts. The optimized acellular isografts and allografts were statistically indistinguishable from the fresh isografts, the fresh allografts, and each other, suggesting that any residual chemicals in the graft did not cause a significant inflammatory response. Thus, histological examination of the levels of CD8+ cells and macrophages that infiltrated the acellular grafts suggested that the decellularization process averted cell-mediated rejection of the grafts.

Optimized Grafts Support Regenerating Axons. The capacity of the optimized acellular graft to support nerve regeneration was tested by examining the growth of axons through the various nerve isografts after 28 and 84 days. All the grafts were isografts, harvested from and implanted into HSD rats. The grafts that were tested included: (1) fresh isografts, (2) optimized acellular grafts, (3) grafts created with the Sondell protocol, and (4) freeze/thaw grafts. This was accomplished by staining longitudinal sections and cross-sections of the grafts for neurofilaments (i.e., cytoskeletal proteins found in axons). At 28 days, new axons had grown completely across the grafts.

FIGS. 8A, 8B and 8C show the Axonal regeneration through acellular nerve grafts was demonstrated by staining longitudinal tissue segments for neurofilaments. The random patterns in the axons at the junctions of the proximal nerve and graft (8A) and the graft and distal nerve (8C) suggest a lack of guidance as the axons crossed into and out of the graft. However, at the midpoint of the graft (8B) the axons were highly aligned, suggesting that they were guided by the extracellular structure of the graft. Suture marks (S) at the nerve/graft junction can be seen in images A and C. Scale bar=100 µm.

The axons appeared to meet some resistance in crossing from the proximal nerve end into the graft and from the graft into the distal nerve end, as demonstrated by the non-linearity in neurofilaments around the suture points on both ends of the graft (FIGS. 8A, 8C). However, once the axons extended into graft, they appeared to grow linearly, as demonstrated by the parallel neurofilaments at the midpoint of the graft (FIG. 8B). Similarly, once the axons found their way into the distal end of the graft, they appeared to grow linearly in the distal direction (data not shown). The same basic pattern was observed in the 84-day acellular nerve grafts. Thus, the optimized acellular nerve grafts supported axonal regeneration and guided the axons toward the distal nerve end.

Optimized Decellularization Process Preserves the ECM. Images of tissue sections stained for laminin allow for the comparison of basal laminae preservation by the decellularization protocols. FIGS. 9A, 9B, 9C and 9D are cross-sections of basal laminae were visualized by the staining of laminin protein. The ring-like appearance of the open tubes in (9A) fresh nerve tissue, (9B) tissue decellularized with the optimized protocol, and (9C) tissue decellularized with the freeze/thaw protocol suggest the preservation of the basal laminae. Rings are difficult to distinguish in (9D) the Sondell treated tissue, suggesting that the basal laminae were damaged during the decellularization treatment. Scale bar=10 µm.

Figure 9A:
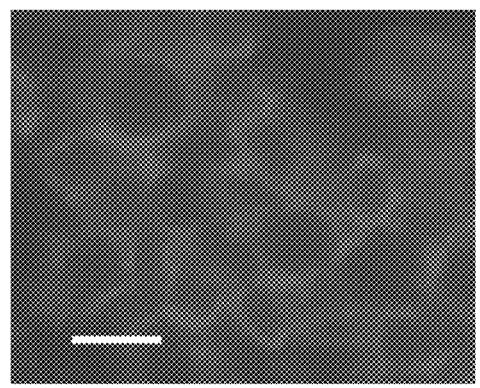
FIGS. 9A, 9B, 9C and 9D are cross-sections of basal laminae were visualized by the staining of laminin protein, the ring-like appearance of the open tubes in (9A) fresh nerve tissue, (9B) tissue decellularized with the optimized protocol, and (9C) tissue decellularized with the freeze/thaw protocol (Scale bar=10 µm)
Figure 9B:
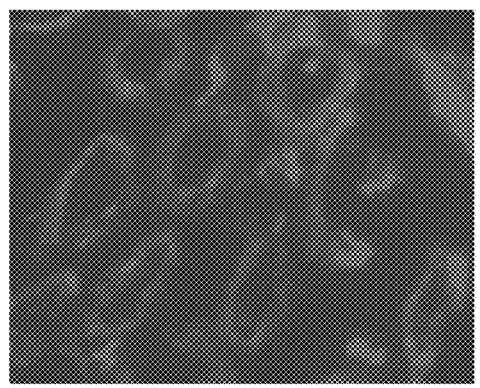
Figure 9C:
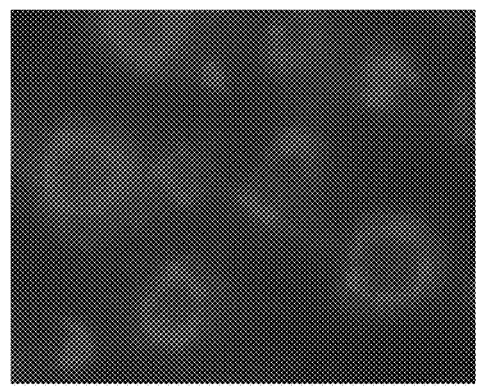
Figure 9D:
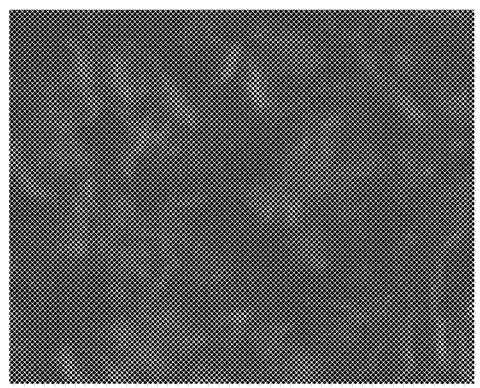

The ring-like structures in native nerve tissue are open columns of basal laminae (FIG. 9A), and similar structures are apparent in the tissue treated with the optimized decellularization protocol (FIG. 9B) and the freeze/thaw protocol (FIG. 9C). In the tissue created with the Sondell treatment (FIG. 9D), the basal laminae appear highly fragmented.

Regenerative Capacity of Optimized Graft Surpasses other Acellular Models. In addition to visually examining the growth of axons through the grafts, axon density at the midpoint of the grafts was determined. The same acellular and fresh isografts that were harvested 28 and 84 days after implantation and sectioned longitudinally were subsequently cross-sectioned at the midpoint of the grafts. The sections were then stained for neurofilaments and the axon density in each section was determined. In the 28 day grafts, the fresh grafts (n=9) and optimized acellular grafts (n=7) were nearly identical with axon densities of 0.9 and 0.98 axons/100 µm2, respectively.

Figure 10A:
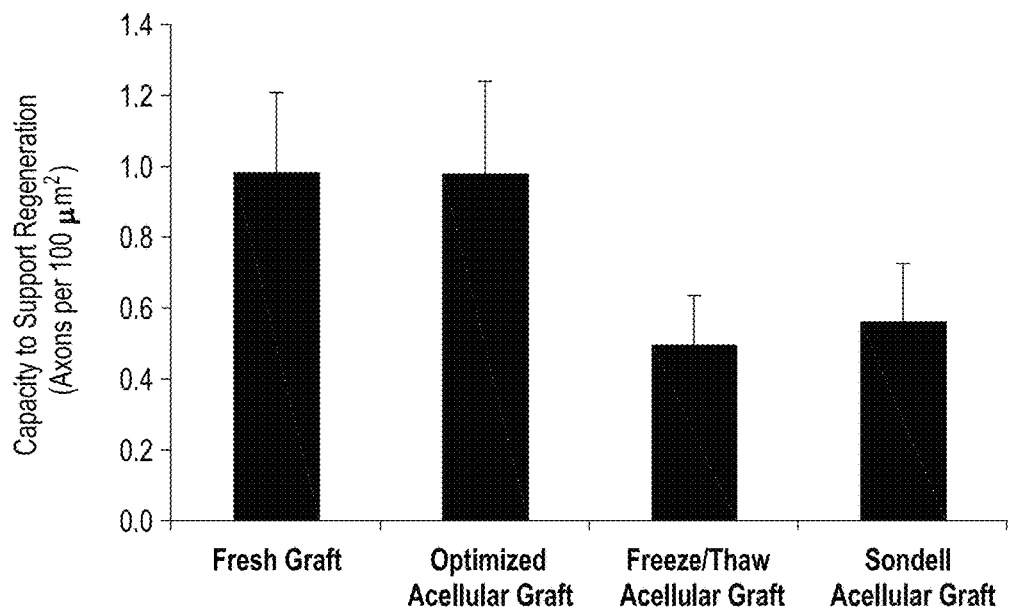
FIGS. 10A and 10B are graphs that show the regenerative capacity of four nerve graft models was evaluated by measuring axon density in cross-sections of the grafts (10A) 28 days after implantation and (10B) 84 days after implantation.
Figure 10B:
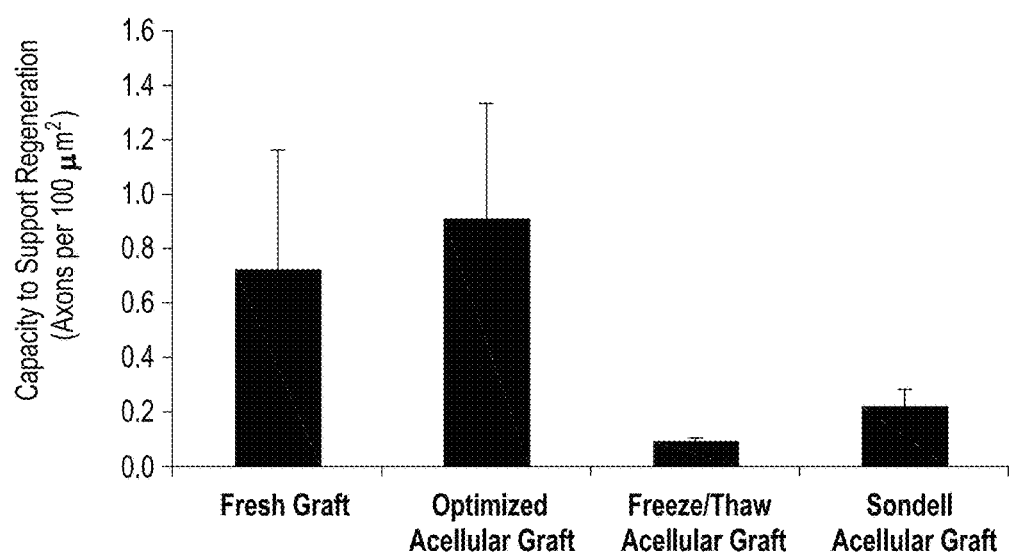

FIGS. 10A and 10B are graphs that show the regenerative capacity of four nerve graft models was evaluated by measuring axon density in cross-sections of the grafts (10A) 28 days after implantation and (10B) 84 days after implantation. Fresh isografts served as a model for the autograft (positive control). Axon density in the fresh grafts and the optimized acellular grafts was statistically indistinguishable. Freeze/thaw grafts had the lowest axon density, implying that the presence of cellular debris may reduce the regenerative capacity of an acellular graft. The Sondell grafts also demonstrated a statistically lower axon density than the optimal acellular grafts, suggesting that preservation of the ECM increased the regenerative capacity of acellular grafts.

The freeze/thaw grafts (n=5) had 0.50 axons/100 µm2, and the Sondell grafts (n=6) had 0.69 axons/100 µm2. Axon density in the freeze/thaw grafts was statistically lower than in the fresh grafts and the optimized acellular grafts (p<<0.01). The axon density in the Sondell grafts was also statistically lower than in the fresh grafts (p<0.01) and the optimized acellular grafts (p<0.05).

For the grafts harvested after 84 days, the fresh grafts (n=5) and optimized acellular grafts (n=5) were again not statistically different, with axon densities of 0.73 and 0.92 axons/100 µm2, respectively (FIG. 10B). The freeze/thaw grafts (n=3) had 0.10 axons/100 µm2, and the Sondell grafts (n=3) had 0.23 axons/100 µm2. Axon density in the freeze/thaw grafts was statistically lower than in the fresh grafts (p<0.05) and the optimized acellular grafts (p<0.05). The axon density in the Sondell grafts was not statistically lower than in the fresh grafts, but was statistically lower than in the optimized acellular grafts (p<0.05).

Since cellular debris is not removed by the freeze/thaw decellularization process and the ECM is damaged by the Sondell decellularization process, the higher axon densities at 24 and 84 days in the optimized acellular grafts suggest that removing cellular debris and preserving the ECM in acellular nerve grafts improve the regenerative capacity of the grafts.

An alternative method for treating severed peripheral nerves is needed to avoid the requirement of multiple surgeries, donor site morbidity, and other drawbacks associated with the autograft. Acellular nerve grafts are derived from donor nerve tissue, so they are composed of proteins endogenous to nerve tissue. Because of their natural composition and the fact that axons preferentially grow through the basal lamina tubes found in nerve tissue, acellular nerve grafts exhibit potential for use as a next generation nerve graft. The present inventors found that improving the decellularization process to yield a better-preserved ECM leads to an improvement in regeneration. However, in order for the optimized acellular grafts to be used clinically, they must also be immunologically tolerated. As discussed hereinabove, a method of removing the cellular material responsible for immunological rejection was developed that also preserved the ECM of nerve tissue. The grafts created with the optimized decellularization treatment were studies in vivo to determine if they are in fact immunologically tolerated and how well they support nerve regeneration.

Cellular antigens are predominantly responsible for the immunological rejection associated with nerve allografts, particularly the antigens associated with Schwann cells, endothelial cells and macrophages. The removal of cellular components from the graft by the optimized protocol was correlated with the immunological response of a host animal of a different strain than the donor animal. The major histocompatibility complex (MHC) of the rat is called RT1 and is highly polymorphic. Rat strains can be characterized by their RT1 haplotype (e.g., RT1b, RTd, RT1l). Matching of haplotypes plays a predominant role in allograft survival. Gulati, et al., demonstrated that in allografts involving stains of different RT1 haplotypes, the increased presence of immune cells associated with rejection was readily detectable at 28 days. Thus, fresh nerve tissue from an HSD rat (RT1b) implanted into a Lewis rat (RT1l) (i.e., a fresh allograft) should display signs of immunological rejection after 28 days. Similarly, an acellular allograft should be rejected if the graft contains membrane-bound antigens associated with the RT1 haplotype.

Rat cytotoxic T-cells carry a CD8 cell surface marker (i.e., they are CD8+ cells), and the presence of cytotoxic T-cells is an important indicator of cell-mediated graft rejection. However, a moderate number of CD8+ cells that are not cytotoxic should be present in any nerve graft after 28 days, whether or not it is being rejected. The non-cytotoxic CD8+ cells are a subset of macrophages that are known to invade after sciatic nerve injuries, even in the absence of immunological rejection. Macrophages are immune cells that respond to nerve injury, clear cellular debris during nerve degeneration, and support regeneration by inducing and producing growth factors. In the case of a rejected allograft, higher numbers of macrophages should be present. However, macrophages also respond to other cues in the regenerating nerve, so an increase in macrophages without a concomitant increase in CD8+ cells does not indicate rejection. Thus, the presence of CD8+ and macrophage cells was anticipated in all four grafts being tested. A statistically significant increase in both CD8+ and macrophage cells in a graft, when compared to a fresh isograft, however, would indicate that the graft was undergoing cell-mediated rejection.

It was found that fresh allografts did exhibit a statistical increase in both CD8+ cells and macrophages, compared to fresh isografts (FIGS. 5 and 7). The acellular grafts did not show any increase in CD8+ cells, compared to fresh isografts, indicating that they did not elicit cell-mediated immune rejection. If residual cellular antigens in the acellular grafts were eliciting cell-mediated rejection, the acellular allografts should have demonstrated a higher level of CD8+ cells than the acellular isografts. Similarly, the level of macrophages in the acellular allografts should have been higher than that in the acellular isografts if the allografts were being rejected. Because the levels of immune cells (i.e., both CD8+ cells and macrophages) in the acellular isografts and allografts were similar to one another, the acellular grafts were not undergoing immunological rejection.

Macrophage invasion into the acellular grafts did appear to be slightly higher than that in the fresh isografts, though not significantly. One possible cause for the elevation in the level of macrophages in the acellular grafts compared to the fresh isografts is that the open basal lamina tubes and the absence of myelin allowed a higher number of macrophages to invade and remain inside the acellular grafts. This may be beneficial since macrophages produce growth factors. In summary, by removing cellular components from nerve tissue, the antigens that would normally initiate cell-mediated immunological rejection of an allograft were removed, and the acellular grafts were immunologically tolerated after 28 days in vivo.

Regenerative Capacity Correlates to Graft Structure and Content. When engineering the optimized acellular grafts, the two major goals were to remove cellular material and to provide structural support for regenerating nerves. Accomplishing those two goals led to improved levels of regeneration in comparison to the levels seen with other acellular grafts. The importance of structural support was evident with histological examination of longitudinal tissue sections. Axons grew linearly in regions of defined structure (e.g., in the nerve graft and distal nerve cable), but their path was irregular in the regions where the graft was attached to the nerve ends (FIGS. 8A-8C). The irregular patterns were potentially caused by the misalignment of basal laminae at the junctions between the nerve ends and the graft. As the axons crossed into and out of the graft, they had to find new basal laminae to provide them with guidance.

In addition to providing guidance, the optimized acellular grafts also supported higher axon densities after 24 and 84 days than the other published acellular graft models (FIGS. 10A and 10B). The lowest axon densities were found in the freeze/thaw grafts. While the structural preservation in the freeze/thaw grafts was similar to that in the optimized grafts (FIGS. 9A-9D), the freeze/thaw procedure was the only decellularization procedure that did not wash dead cells out of the grafts. Thus, a correlation was suggested between the presence of cell debris and a reduction in the level of nerve regeneration. The primary difference between the Sondell protocol and the optimized decellularization protocol was preservation of the ECM (FIGS. 9A-9D). Consequently, the higher axon density in the optimized acellular grafts suggests that providing regenerating axons with an ECM structure that mimics that of native nerve is important for maximizing regeneration in an acellular graft. The importance of these factors appears to become more evident over longer time periods, with the optimized graft demonstrating axon densities 910% higher than the freeze/thaw graft and 401% higher than the Sondell graft after 84 days.

Since fresh isografts were the only grafts that contained living cells (e.g., Schwann cells and macrophages) that aid regeneration, they were expected to support higher axon densities than any of the acellular grafts. However, the data suggest that in 10 mm nerve grafts, the combination of desirable structure and the removal of cellular debris were sufficient to attain axon densities statistically indistinguishable from those in fresh isografts (FIGS. 10A and 10B). In the case of longer grafts, however, the need for support cells will probably become more crucial. To address injuries with longer gaps, cells (e.g., Schwann cells) may be incorporated into the optimized acellular grafts prior to implantation.

Because the optimized acellular graft disclosed herein is a simpler system than the autograft, it serves as a tool to study individual cells or growth factors by selectively incorporating them into the graft. The natural structural environment of this acellular graft makes it an ideal model for conducting such experiments. As more information is gained about the role of the ECM, support cells, and growth factors, better therapeutic systems may be engineered for stimulating nerve regeneration and an off-the-shelf replacement for the autograft can be developed, possibly using this graft as the structural foundation.

While specific alternatives to steps of the invention have been described herein, additional alternatives not specifically disclosed, but known within the art, are intended to fall within the scope of the present invention. Thus it is understood that other applications of the present invention will be apparent to those skilled in the art upon the reading of the described embodiments and a consideration of the claims and drawings.

REFERENCES

1. Lundborg, G. (2000) A 25-year perspective of peripheral nerve surgery: evolving neuroscientific concepts and clinical significance. *J Hand Surg [Am]* 25, 391.
2. Hudson, T. W., Evans, G. R., and Schmidt, C. E. (2000) Engineering strategies for peripheral nerve repair. *Orthop Clin North Am* 31, 485.
3. Strauch, B. (2000) Use of nerve conduits in peripheral nerve repair. *Hand Clin* 16, 123.
4. Gulati, A. K., Rai, D. R., and Ali, A. M. (1995) The influence of cultured Schwann cells on regeneration through acellular basal lamina grafts. *Brain Res* 705, 118.
5. Sorensen, J., Fugleholm, K., Moldovan, M., Schmalbruch, H., and Krarup, C. (2001) Axonal elongation through long acellular nerve segments depends on recruitment of phagocytic cells from the near-nerve environment. Electrophysiological and morphological studies in the cat. *Brain Res* 903, 185.
6. Frostick, S. P., Yin, Q., and Kemp, G. J. (1998) Schwann cells, neurotrophic factors, and peripheral nerve regeneration. *Microsurgery* 18, 397.
7. Ide, C., Osawa, T., and Tohyama, K. (1990) Nerve regeneration through allogeneic nerve grafts, with special reference to the role of the Schwann cell basal lamina. *Prog Neurobiol* 34, 1.
8. Martini, R. (1994) Expression and functional roles of neural cell surface molecules and extracellular matrix components during development and regeneration of peripheral nerves. *J Neurocytol* 23, 1.
9. Fawcett, J. W., and Keynes, R. J. (1990) Peripheral nerve regeneration. *Annu Rev Neurosci* 13, 43.
10. Ide, C., et al. (1998) Long acellular nerve transplants for allogeneic grafting and the effects of basic fibroblast growth factor on the growth of regenerating axons in dogs: a preliminary report. *Exp Neurol* 154, 99.
11. Sondell, M., Lundborg, G., and Kanje, M. (1998) Regeneration of the rat sciatic nerve into allografts made acellular through chemical extraction. *Brain Res* 795, 44.
12. Gulati, A. K., and Cole, G. P. (1994) Immunogenicity and regenerative potential of acellular nerve allografts to repair peripheral nerve in rats and rabbits. *Acta Neurochir (Wien)* 126, 158.
13. Zalewski, A. A., and Gulati, A. K. (1982) Evaluation of histocompatibility as a factor in the repair of nerve with a frozen nerve allograft. *J Neurosurg* 56, 550.
14. Danielsen, N., Kerns, J. M., Holmquist, B., Zhao, Q., Lundborg, G., and Kanje, M. (1995) Predegeneration enhances regeneration into acellular nerve grafts. *Brain Res* 681, 105.
15. Osawa, T., Tohyama, K., and Ide, C. (1990) Allogeneic nerve grafts in the rat, with special reference to the role of Schwann cell basal laminae in nerve regeneration. *J Neurocytol* 19, 833.
16. Pollard, J. D., and Fitzpatrick, L. (1973) An ultrastructural comparison of peripheral nerve allografts and autografts. *Acta Neuropathol (Berl)* 23, 152.
17. Hall, S. M. (1986) Regeneration in cellular and acellular autografts in the peripheral nervous system. *Neuropathol Appl Neurobiol* 12, 27.
18. Krekoski, C. A., Neubauer, D., Zuo, J., and Muir, D. (2001) Axonal regeneration into acellular nerve grafts is enhanced by degradation of chondroitin sulfate proteoglycan. *J Neurosci* 21, 6206.
19. Johnson, P. C., Duhamel, R. C., Meezan, E., and Brendel, K. (1982) Preparation of cell-free extracellular matrix from human peripheral nerve. *Muscle Nerve* 5, 335.
20. Gulati, A. K., and Cole, G. P. (1990) Nerve graft immunogenicity as a factor determining axonal regeneration in the rat. *J Neurosurg* 72, 114.
21. Gulati, A. K. (1988) Evaluation of acellular and cellular nerve grafts in repair of rat peripheral nerve. *J Neurosurg* 68, 117.
22. National Center for Health Statistics Based on Classification of Diseases, 9th Revision, Clinical Modifications for the Following Categories: ICD-9 CM Codes 04.3, 04.5, 04.6, 04.7.
23. Pollard, J. D., and McLeod, J. G. (1981) Fresh and predegenerate nerve allografts and isografts in trembler mice. *Muscle Nerve* 4, 274.
24. Gulati, A. K. (1998) Immune response and neurotrophic factor interactions in peripheral nerve transplants. *Acta Haematol* 99, 171.
25. Guenther, E., Stark, O. (1977) The major histocompatibility system of the rat (Ag-B or H-1 system), in: D. Goetze, ed. The major histocompatibility system in man and animals. Springer-Verlag, New Yok, pp. 207-253.
26. Jander, S., Lausberg, F., and Stoll, G. (2001) Differential recruitment of CD8+ macrophages during Wallerian degeneration in the peripheral and central nervous system. *Brain Pathol* 11, 27.
27. Hirata, K., Mitoma, H., Ueno, N., He, J. W., and Kawabuchi, M. (1999) Differential response of macrophage subpopulations to myelin degradation in the injured rat sciatic nerve. *J Neurocytol* 28, 685.
28. Bruck, W. (1997) The role of macrophages in Wallerian degeneration. *Brain Pathol* 7, 741.
29. Perry, V. H., and Brown, M. C. (1992) Macrophages and nerve regeneration. *Curr Opin Neurobiol* 2, 679.
30. Pollard, J. D., and Fitzpatrick, L. (1973) A comparison of the effects of irradiation and immunosuppressive agents on regeneration through peripheral nerve allografts: an ultrastructural study. *Acta Neuropathol (Berl)* 23, 166.

What is claimed is:
1. A method for preparing a native, nerve cell-free tissue replacement nerve graft comprising the steps of:
   soaking the nerve graft for at least six hours in a solution comprising sulfobetaine;

washing the nerve graft in one or more solutions of a buffered salt;

extracting the nerve graft in a mixture of one or more sulfobetaines with an anionic surface-active detergent; and washing the nerve graft in one or more solutions of a buffered salt to remove the excess anionic surface-active detergent, wherein the nerve graft is immunologically tolerated when implanted.

2. The method of claim 1, further comprising the step of:
adhering one or more components to the nerve graft before storing, wherein the components are selected from the group consisting of a cell, a polymer, a bioactive compound, and combinations thereof.

3. The method of claim 2, wherein the cells are obtained from a donor, a host, from cell culture from a donor or a host, or cell cultures of established cells, tissue cells, or transformed cell lines.

4. The method of claim 2, wherein the bioactive compound is selected from the group consisting of a drug, protein, peptide, polysaccharide, fatty acid, nucleic acid, oligonucleotide, detectable agent, organic molecules, inorganic molecules or salts and combinations thereof that include natural or synthetic analogs, derivatives, or mimetic versions of the bioactive compound for therapeutic, prophylactic and diagnostic purposes.

5. The method of claim 2, wherein the polymer is selected from the group consisting of naturally occurring, synthetically-derived, covalently crosslinkable, ionically crosslinkable, hydrophilic, and combinations thereof.

6. The method of claim 1, wherein the nerve graft is further modified into a structure selected from the group consisting of a suture, tube, sheet, film, scaffold, valve, limb replacement, tissue transplant, and joint for delivery into the body.

7. The method of claim 1, wherein the step of washing the nerve graft tissue replacement comprises serial solutions of a buffered salt comprises three serial washes of 100 mM sodium and 50 mM phosphate for about 15 minutes each.

8. The method of claim 1, wherein the nerve graft is harvested from mammalian cadaver.

9. The method of claim 8, wherein the nerve graft is cleaned of fat and blood after harvesting and rinsed for several hours in deionized distilled water.

10. A native, neural cell-free tissue replacement nerve graft made by the method of:
soaking the nerve graft for at least six hours in a solution comprising one or more sulfobetaines;
washing the nerve graft in one or more solutions of a buffered salt;
extracting the nerve graft in a mixture of one or more sulfobetaines with an anionic surface-active detergent; and
washing the nerve graft in one or more solutions of a buffered salt to remove the excess anionic surface-active detergent, wherein the nerve graft is immunologically tolerated when implanted.

11. The cell-free neural tissue replacement of claim 10, further comprising the step of:
adhering one or more components to the nerve graft before storing, wherein the components are selected from the group consisting of a cell, a polymer, a bioactive compound, and combinations thereof.

12. The cell-free neural tissue replacement of claim 11, wherein the cell is selected from the group consisting of bone, cartilage, dermal, muscular, thyroidal, parathyroidal, lymphoid, pancreatic, urinary, digestive, hepatic, biliary, vascular, nervous, reproductive and combinations thereof.

13. The cell-free neural tissue replacement of claim 11, wherein the cells are obtained from a donor, a host, from cell culture from a donor or a host, or cell cultures of established cells, tissue cells, or transformed cell lines.

14. The cell-free neural tissue replacement of claim 11, wherein the bioactive compound is selected from the group consisting of a drug, protein, peptide, polysaccharide, fatty acid, nucleic acid, oligonucleotide, detectable agent, organic molecules, inorganic molecules or salts and combinations thereof that include natural or synthetic analogs, derivatives, or mimetic versions of the bioactive compound for therapeutic, prophylactic and diagnostic purposes.

15. The cell-free neural tissue replacement of claim 11, wherein the polymer is selected from the group consisting of naturally occurring, synthetically-derived, covalently crosslinkable, ionically crosslinkable, hydrophilic, and combinations thereof.

16. The cell-free neural tissue replacement of claim 10, wherein the nerve graft is further modified into a structure selected from the group consisting of a suture, tube, sheet, film, scaffold, valve, limb replacement, tissue transplant, and joint for delivery into the body.

17. The cell-free neural tissue replacement of claim 10, wherein the step of washing the tissue replacement comprises serial solutions of a buffered salt comprises three serial washes of 100 mM sodium and 50 mM phosphate for about 15 minutes each.

18. The cell-free neural tissue replacement of claim 10, wherein the nerve graft is harvested from mammalian cadaver.

19. The cell-free neural tissue replacement of claim 18, wherein the nerve graft is cleaned of fat and blood after harvesting and rinsed for several hours in deionized distilled water.

20. An optimized acellular nerve graft that supports axonal regeneration, guides the axons toward the distal nerve end and is immunologically tolerated, wherein the nerve graft is made by the method of soaking the nerve graft for at least six hours in a solution comprising one or more sulfobetaines;
washing the nerve graft in one or more solutions of a buffered salt;
extracting the nerve graft in a mixture of one or more sulfobetaines with an anionic surface-active detergent; and
washing the nerve graft in one or more solutions of a buffered salt to remove the excess anionic surface-active detergent, wherein the acellular neural graft, is immunologically tolerated when implanted.

21. The acellular graft of claim 20, further comprising the step of adhering one or more components to the neural graft before storing.

22. The acellular graft of claim 20, further comprising a component selected from the group consisting of a cell, a polymer, a bioactive compound or combinations thereof.

23. The acellular graft of claim 20, wherein the neural graft is stored at about 4 degrees centigrade in a sterile, buffered solution until use.

24. The method of claim 1, wherein the nerve graft is an autograft, allograft, or xenograft.

25. The acellular nerve graft of claim 20, wherein the nerve graft is an autograft, allograft, or xenograft.

26. A method for preparing a native, nerve cell-free tissue replacement nerve graft comprising the steps of:

soaking the nerve graft for at least six hours in a solution comprising sulfobetaine;
washing the nerve graft in one or more solutions of a buffered salt;
extracting the nerve graft in a mixture of one or more sulfobetaines with an anionic surface-active detergent;
washing the nerve graft in one or more solutions of a buffered salt to remove the excess anionic surface-active detergent, wherein the nerve graft is immunologically tolerated when implanted; and
adhering one or more components to the nerve graft before storing, wherein the components are selected from the group consisting of a cell, a polymer, a bioactive compound, and combinations thereof, wherein the cells are obtained from a donor, a host, from cell culture from a donor or a host, or cell cultures of established cells, tissue cells, or transformed cell lines.

* * * * *